(12) United States Patent
Howard

(10) Patent No.: US 10,576,272 B2
(45) Date of Patent: *Mar. 3, 2020

(54) HIGH FREQUENCY STIMULATION OF THE SPINAL CORD FROM INSIDE THE DURA

(71) Applicant: University of Iowa Research Foundation, Iowa City, IA (US)

(72) Inventor: Matthew A. Howard, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/118,151

(22) Filed: Aug. 30, 2018

(65) Prior Publication Data

US 2018/0369577 A1    Dec. 27, 2018

Related U.S. Application Data

(60) Continuation of application No. 15/437,803, filed on Feb. 21, 2017, now Pat. No. 10,071,240, which is a
(Continued)

(51) Int. Cl.
*A61N 1/05* (2006.01)
*A61N 1/36* (2006.01)

(52) U.S. Cl.
CPC ......... *A61N 1/0553* (2013.01); *A61N 1/0556* (2013.01); *A61N 1/0558* (2013.01);
(Continued)

(58) Field of Classification Search
CPC .. A61N 1/0553; A61N 1/0556; A61N 1/0558; A61N 1/36071; A61N 1/36171
See application file for complete search history.

(56) References Cited

U.S. PATENT DOCUMENTS

| 3,612,061 A | 10/1971 | Collins et al. |
| 3,724,467 A | 4/1973 | Avery et al. |

(Continued)

FOREIGN PATENT DOCUMENTS

| CN | 101048194 | 10/2007 |
| EP | 1048317 | 11/2000 |

(Continued)

OTHER PUBLICATIONS

U.S. Appl. No. 12/130,138, Decision on Appeal mailed on Dec. 2, 2016, 19 pages.
(Continued)

*Primary Examiner* — Paula J Stice
(74) *Attorney, Agent, or Firm* — Kilpatrick Townsend & Stockton LLP

(57) ABSTRACT

This invention provides a device for implantation directly into the spinal cord for the purpose of treating back pain. Electrodes on a backing that conforms directly to the spinal cord are installed as a source of electrical stimulation and pain relief. The floating electrodes can be flexibly mounted to the substrate such that when the electrode array is implanted into the subject, individual electrodes float or move resiliently relative to the substrate to an extent sufficient to accommodate pulsations of the surface of the spinal cord within the dura.

20 Claims, 27 Drawing Sheets

Figure 1A:
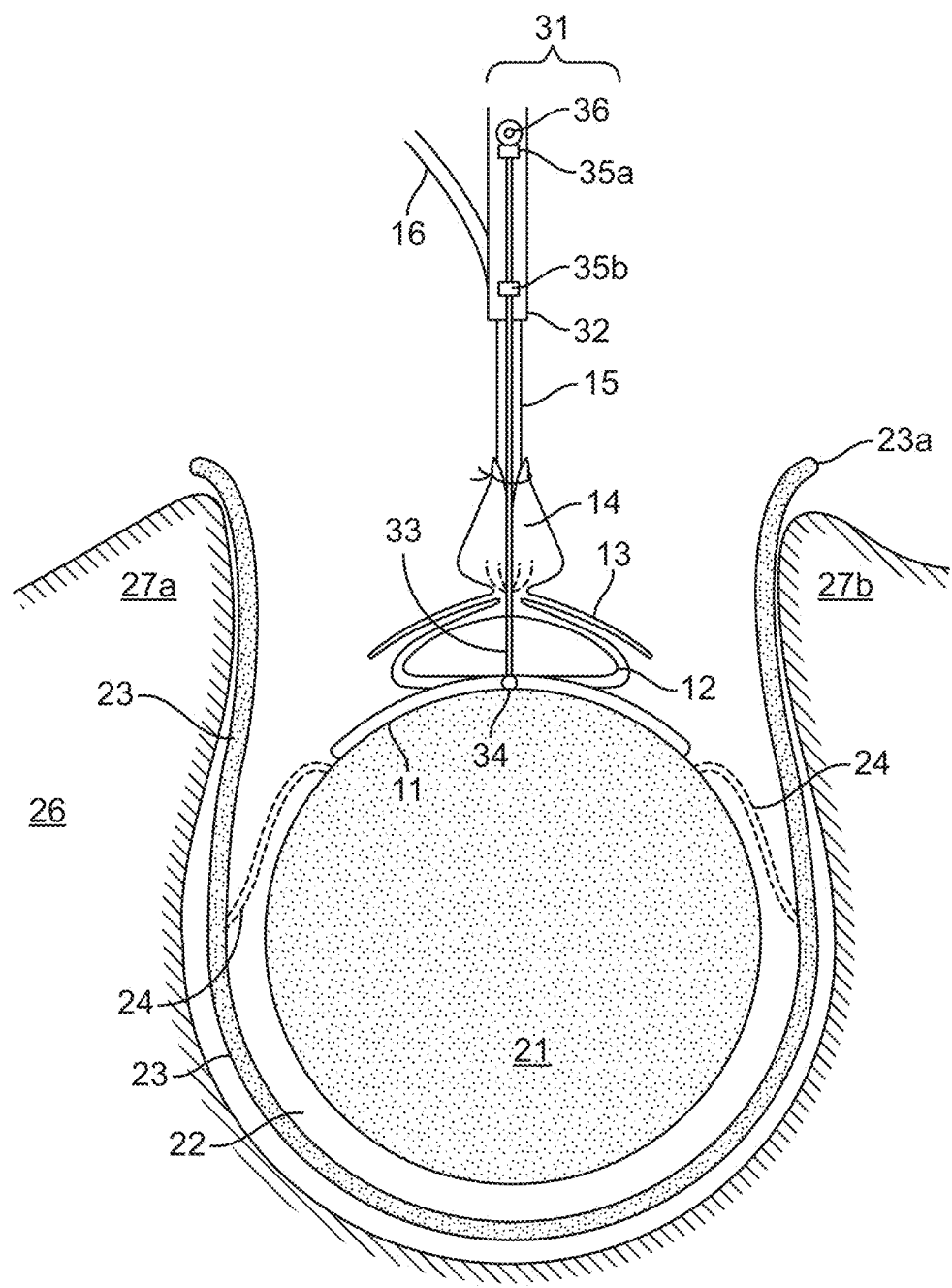

Related U.S. Application Data continuation-in-part of application No. 15/004,515, filed on Jan. 22, 2016, now Pat. No. 9,572,976, which is a division of application No. 14/375,781, filed as application No. PCT/US2013/023912 on Jan. 30, 2013, now Pat. No. 9,254,379, said application No. 15/437,803 is a continuation-in-part of application No. 15/267,765, filed on Sep. 16, 2016, now abandoned, which is a continuation of application No. 14/821,540, filed on Aug. 7, 2015, now Pat. No. 9,486,621, which is a division of application No. 13/885,157, filed as application No. PCT/US2011/060462 on Nov. 11, 2011, now Pat. No. 9,364,660, said application No. 15/437,803 is a continuation-in-part of application No. 15/191,214, filed on Jun. 23, 2016, now Pat. No. 9,950,165, which is a continuation of application No. 14/375,785, filed as application No. PCT/US2013/023897 on Jan. 30, 2013, now Pat. No. 9,403,008, said application No. 15/437,803 is a continuation-in-part of application No. 14/916,892, filed as application No. PCT/US2014/054243 on Sep. 5, 2014, now abandoned.

(60) Provisional application No. 61/592,515, filed on Jan. 30, 2012, provisional application No. 61/592,520, filed on Jan. 30, 2012, provisional application No. 61/412,651, filed on Nov. 11, 2010, provisional application No. 61/874,340, filed on Sep. 5, 2013.

(52) U.S. Cl.
CPC ..... *A61N 1/36071* (2013.01); *A61N 1/36171* (2013.01); *F04C 2270/0421* (2013.01)

(56) References Cited

U.S. PATENT DOCUMENTS

| | | | |
|---|---|---|---|
| 3,822,708 A | 7/1974 | Zilber | |
| 4,549,556 A | 10/1985 | Tarjan et al. | |
| 4,590,946 A | 5/1986 | Loeb | |
| 4,837,049 A | 6/1989 | Byers et al. | |
| 6,175,769 B1 | 1/2001 | Errico et al. | |
| 6,295,472 B1 | 9/2001 | Rubinstein et al. | |
| 6,319,241 B1 | 11/2001 | King et al. | |
| 6,549,810 B1 | 4/2003 | Leonard et al. | |
| 6,631,295 B2 | 10/2003 | Rubinstein et al. | |
| 7,333,857 B2 | 2/2008 | Campbell | |
| 7,337,006 B2 | 2/2008 | Kim et al. | |
| 7,769,472 B2 | 8/2010 | Gerber | |
| 8,170,675 B2 | 5/2012 | Alataris et al. | |
| 8,209,021 B2 | 6/2012 | Alataris et al. | |
| 8,255,057 B2 | 8/2012 | Fang et al. | |
| 8,295,945 B1 | 10/2012 | Thacker et al. | |
| 8,649,874 B2 | 2/2014 | Alataris et al. | |
| 8,712,533 B2 | 4/2014 | Alataris et al. | |
| 8,838,248 B2 | 9/2014 | Walker et al. | |
| 8,892,209 B2 | 11/2014 | Alataris et al. | |
| 9,254,379 B2 | 2/2016 | Howard et al. | |
| 9,364,660 B2 | 6/2016 | Howard et al. | |
| 9,403,008 B2 | 8/2016 | Howard | |
| 9,486,621 B2 | 11/2016 | Howard et al. | |
| 9,572,976 B2 | 2/2017 | Howard et al. | |
| 10,071,240 B2 | 9/2018 | Howard et al. | |
| 2002/0111660 A1 | 8/2002 | Errico et al. | |
| 2002/0111668 A1 | 8/2002 | Smith | |
| 2003/0014080 A1 | 1/2003 | Baudino et al. | |
| 2003/0204228 A1 | 10/2003 | Cross et al. | |
| 2004/0162594 A1 | 8/2004 | King et al. | |
| 2004/0176831 A1 | 9/2004 | Gliner et al. | |
| 2005/0131506 A1 | 6/2005 | Rezai et al. | |
| 2006/0052826 A1* | 3/2006 | Kim | A61N 1/0558 607/2 |
| 2006/0074456 A1* | 4/2006 | Pyles | A61N 1/36007 607/40 |
| 2006/0173522 A1 | 8/2006 | Osorio | |
| 2007/0055332 A1 | 3/2007 | Swoyer | |
| 2007/0073357 A1 | 3/2007 | Rooney et al. | |
| 2008/0234791 A1 | 9/2008 | Arle et al. | |
| 2009/0281599 A1 | 11/2009 | Thacker et al. | |
| 2010/0057177 A1 | 3/2010 | Moffitt et al. | |
| 2010/0057178 A1 | 3/2010 | Simon et al. | |
| 2010/0063568 A1 | 3/2010 | Staunton et al. | |
| 2010/0100165 A1 | 4/2010 | Swanson et al. | |
| 2010/0105987 A1 | 4/2010 | Miles et al. | |
| 2010/0145428 A1 | 6/2010 | Cameron et al. | |
| 2010/0204766 A1 | 8/2010 | Zdeblick et al. | |
| 2010/0274312 A1* | 10/2010 | Alataris | A61N 1/36071 607/46 |
| 2011/0184488 A1 | 7/2011 | De et al. | |
| 2011/0224755 A1 | 9/2011 | Arle et al. | |
| 2012/0016438 A1 | 1/2012 | Alataris et al. | |
| 2012/0283835 A1 | 11/2012 | Bentley et al. | |
| 2014/0128955 A1 | 5/2014 | Howard et al. | |
| 2014/0371830 A1 | 12/2014 | Howard et al. | |
| 2014/0379043 A1 | 12/2014 | Howard | |
| 2015/0005680 A1 | 1/2015 | Lipani | |
| 2016/0213917 A1 | 7/2016 | Dalm et al. | |
| 2017/0028201 A1 | 2/2017 | Howard | |
| 2017/0065814 A1 | 3/2017 | Howard et al. | |

FOREIGN PATENT DOCUMENTS

| | | |
|---|---|---|
| WO | 9532677 | 12/1995 |
| WO | 03063949 | 8/2003 |
| WO | 2006029257 | 3/2006 |
| WO | 2010124139 | 10/2010 |
| WO | 2012065125 | 5/2012 |
| WO | 2013116368 | 8/2013 |
| WO | 2013116377 | 8/2013 |

OTHER PUBLICATIONS

Simon et al., Regulation of Cerebrospinal Fluid (CSF) Flow in Neurodegenerative, Neurovascular and Neuroinflammatory Disease, Biochim. Biophys. Acta., vol. 1862, No. 3, Mar. 2016, pp. 442-451.
Troyka et al., Quick Access: Reference for Writers, MLA Update, 8th Edition, Chapter 60 Articles, 2017, pp. 479-483.
Whedon et al., Cerebrospinal Fluid Stasis and its Clinical Significance, Altern. Ther. Health Med., vol. 15, No. 3, May-Jun. 2009, pp. 54-60.
About Nevro website: http://www.nevro.com/about-us/who-we-are/, Sep. 22, 2015, 1 page.
High-Frequency Spinal Cord Stimulation, Nevro pamphlet, 2012004 Rev. D, 4 pages.
Nevro Corp. Announces Publication of Positive Six-Month Clinical Data for Senza® HF10™ High-Frequency Spinal Cord Stimulation Therapy in Europe, http://www.nevro.com/German/Presse/Pressemeldungen/Pressemitteilung-Details/2013/Nevro-Corp-Announces-Publication-of-Positive-Six-Month-Clinical-Data-for-Senza-HF10-High-Frequency-Spinal-Cord-Stimulation-Therapy-in-Europe/default.aspx, Feb. 6, 2013, 2 pages.
Burton, "Safety and clinical efficacy of implanted neuroaugmentive spinal devices for the relief of pain", Appl. Neurophysiol. vol. 40, No. 2-4, 1977-1978, pp. 175-183.
Eldabe et al., "An analysis of the components of pain, function, and health-related quality of life in patients with failed back surgery syndrome treated with spinal cord stimulation or conventional medical management", Neuromodulation, vol. 13, No. 3, Jul. 2010, pp. 201-209.
EP11839545.8, "Extended European Search Report", dated Apr. 24, 2014, 7 pages.
EP13743674.7, "Supplementary European Search Report," dated Sep. 25, 2015, 5 pages.
Holsheimef et al., "Spinal geometry and paresthesia coverage in spinal cord stimulation", Neuromodulation, vol. 1, No. 3, 1998, pp. 129-136.

(56) References Cited

OTHER PUBLICATIONS

Holsheimer, "Computer modelling of spinal cord stimulation and its contribution to therapeutic efficacy", Spinal Cord, vol. 36, 1998, pp. 531-540.
Holsheimer et al., "Effects of electrode positioning on perception threshold and paresthesia coverage in spinal cord stimulation", Neuromodulation, vol. 10, No. 1, Jan. 2007, pp. 34-41.
Holsheimer et al., "Optimum electrode geometry for spinal cord stimulation: the narrow bipole and tripole", Med Biol Eng Comput., vol. 35, No. 5, Sep. 1997, pp. 493-497.
Holsheimer et al., "Which Neuronal Elements are Activated Directly by Spinal Cord Stimulation", Neuromodulation., vol. 5, No. 1, 2002, pp. 25-31.
Flouty et al., "A new device concept for directly modulating spinal cord pathways: initial in vivo experimental results", Physiol. Meas., vol. 33, No. 12, 2012, pp. 2003-2015.
Flouty et al., "Intracranial somatosensory responses with direct spinal cord stimulation in anesthetized sheep", PLoS One, vol. 8, No. 2, Feb. 2013, pp. 1-11.
Gibson-Corley et al., "Ovine Tests of a Novel Spinal Cord Neuromodulator and Dentate Ligament Fixation Method", Journal of Investigative Surgery 25(6), 2012, pp. 366-374.
Gibson-Corley et al., "Postsurgical Pathologies Associated with Intradural Electrical Stimulation in the Central Nervous System: Design Implications for a New Clinical Device", BioMed Research International vol. 2014, Article ID 989175,, 2014, 10 pages.
Gildenberg, "Evolution of Spinal Cord Surgery for Pain", Clinical Neurosurgery, vol. 53, 2006, pp. 11-17.
Howell et al., "Evaluation of intradural stimulation efficiency and selectivity in a computational model of spinal cord stimulation", PLoS One, vol. 9, No. 12, Dec. 23, 2014, pp. 1-25.
Huang et al., "Comparison of spinal cord stimulation profiles from intra- and extradural electrode arrangements by finite element modelling", Med Biol Eng Comput., vol. 52, No. 6, Jun. 2014, pp. 531-538.
Long, "Electrical Stimulation for the Control of Pain", Symposium on Pain, Arch Surg., vol. 112, No. 7, Jul. 1977, pp. 884-888.
Long, "The Current Status of Electrical Stimulation of the Nervous System for the Relief of Chronic Pain", Surg Neural., vol. 49, No. 2, Feb. 1998, pp. 142-144.
Mayfield Clinic & Spine Institut, "Spinal Cord Stimulation, advanced level", http://www.mayfieldclinic.com/PDF/PE-Stim/pdf, 1998-2016, 6 pages.
Oliynyk et al., "Dynamic loading characteristics of an intradural spinal cord stimulator", Journal of Applied Physics, vol. 113, Article 026103, 2013, 3 pages.
Oya et al., "Applier tool for intradural spinal cord implants", J Med Eng Technol., vol. 36, No. 3, Apr. 2012, pp. 169-173.
Oya et al., "Soft-coupling suspension system for an intradural spinal cord stimulator: Biophysical performance characteristics", J. Appl. Phys. vol. 114, Article 164701, 2013, 7 pages.
Oya et al., "Spinal canal surrogate for testing intradural implants", J Med Eng Technol., vol. 36, No. 8, Nov. 2012, pp. 407-410.
PCT/US2011/060462, "International Search Report and Written Opinion", dated Mar. 2, 2012, 18 pages.
PCT/US2013/023897, "International Search Report & Written Opinion", dated Apr. 16, 2013, 12 pages.
PCT/US2013/023912, "International Search Report and Written Opinion", dated Jun. 14, 2013, 16 pages.
PCT/US2014/054243, "International Search Report and Written Opinion", dated Dec. 23, 2014, 13 pages.
PCT/US2011/060462, "International Preliminary Report on Patentability", dated May 14, 2013, 11 pages.
Chinese Office Action dated Sep. 19, 2014 for CN Application No. 201180064806.1, 16 pages.
Safayi et al., "Biomechanical performance of an ovine model of intradural spinal cord stimulation", J Med Eng Technol., vol. 38, No. 5, Jul. 2014, pp. 269-273.
Shealy et al., "Dorsal column electroanalgesia", J Neurosurg., vol. 32, No. 5, May 1970, pp. 560-564.
Song et al., "Power and signal transmission protocol for a contactless subdural spinal cord stimulation device", Biomed Microdevices, vol. 15, No. 1, Feb. 2013, pp. 27-36.
Sweet et al., "Stimulation of the posterior columns of the spinal cord for pain control: indications, technique, and results", Clin Neurosurg, vol. 21, 1974, pp. 278-310.
Viljoen et al., "Apparatus for simulating dynamic interactions between the spinal cord and soft-coupled intradural implants", Rev Sci Instrum., vol. 84, No. 11, Nov. 2013, 7 pages.
Viljoen et al., "MR-based measurement of spinal cord motion during flexion of the spine: implications for intradural spinal cord stimulator systems", J Med Eng Technol., vol. 38, No. 1, 2014, pp. 1-3.
Wilson et al., "Pulsatile spinal cord surrogate for intradural neuromodulation studies", Journal of Medical Engineering and Technology, vol. 36, No. 1, 2012, pp. 22-25.
Notice of Reasons for Rejection dated Dec. 5, 2016 for Japanese Patent Application No. 2014-554972, includes English Translations, 10 pages.

\* cited by examiner

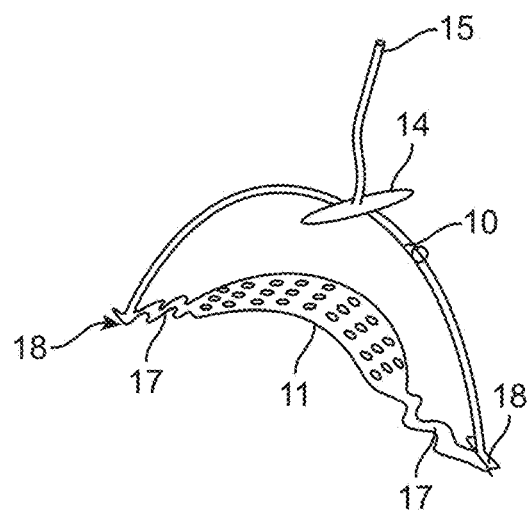
FIG. 7A
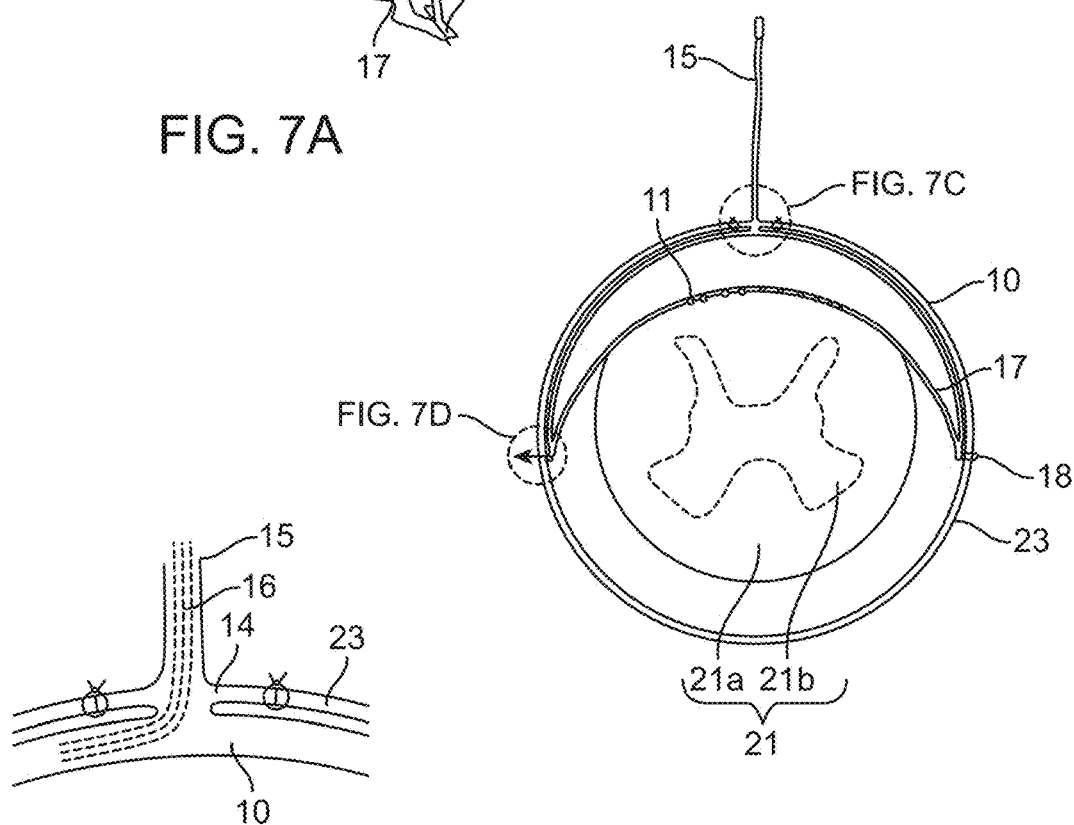
FIG. 7B
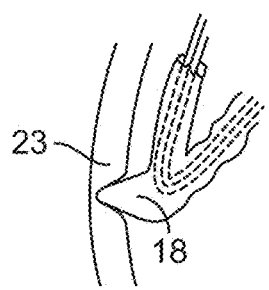
FIG. 7C
FIG. 7D

HIGH FREQUENCY STIMULATION OF THE SPINAL CORD FROM INSIDE THE DURA

REFERENCE TO RELATED APPLICATIONS

This application is a continuation of U.S. patent application Ser. No. 15/437,803, filed on Feb. 21, 2017, issued as U.S. Pat. No. 10,071,240; which is a continuation-in-part of U.S. patent application Ser. No. 15/004,515, filed on Jan. 22, 2016, issued as U.S. Pat. No. 9,572,976; which is a divisional of U.S. Ser. No. 14/375,781, filed on Jul. 30, 2014, issued as U.S. Pat. No. 9,254,379; which is the U.S. National Stage of international Application PCT/US2013/23912, filed Jan. 30, 2013, which was published as WO 2013/116377 on Aug. 8, 2013; which claims the priority benefit of U.S. provisional application 61/592,515, filed Jan. 30, 2012; and U.S. provisional application 61/592,520 filed Jan. 30, 2012.

U.S. patent application Ser. No. 15/437,803, is also a continuation-in-part of U.S. patent application Ser. No. 15/267,765, filed Sep. 16, 2016; which is a continuation of U.S. patent application Ser. No. 14/821,540, filed on Aug. 7, 2015, issued as U.S. Pat. No. 9,486,621; which is a divisional of U.S. patent application Ser. No. 13/885,157, filed on Jan. 6, 2014, issued as U.S. Pat. No. 9,364,660; which is the U.S. National Stage of International Application PCT/US2011/060462, filed on Nov. 11, 2011; which claims the benefit of U.S. Provisional Application No. 61/412,651, filed Nov. 11, 2010.

U.S. patent application Ser. No. 15/437,803, is also a continuation-in-part of U.S. patent application Ser. No. 15/191,214, filed Jun. 23, 2016, issued as U.S. Pat. No. 9,950,165; which is a continuation of U.S. application Ser. No. 14/375,785, filed Jul. 30, 2014, issued as U.S. Pat. No. 9,403,008; which is the U.S. National Stage of International Application PCT/US2013/023897, filed Jan. 30, 2013, which was published as WO 2013/116368 on Aug. 8, 2013; which claims the priority benefit of U.S. provisional application 61/592,520 filed Jan. 30, 2012.

U.S. patent application Ser. No. 15/437,803, is also a continuation-in-part of U.S. patent application Ser. No. 14/916,892, filed Mar. 4, 2016; which is the U.S. National Stage of PCT/US2014/054243, filed Sep. 5, 2014, and published as WO/2015/035135 on Mar. 12, 2015; which claims the priority benefit of U.S. provisional application 61/874,340, filed Sep. 5, 2013.

All the aforelisted priority applications are hereby incorporated herein by reference in their entireties for all purposes.

FIELD OF THE INVENTION

The invention relates generally to the field of medical devices and pain management. In particular, it provides electrode arrays and support structures for electrical stimulation of the spinal cord.

BACKGROUND

Chronic pain is an often unbearable sequelae of spinal cord injury or disease. It can interfere with the basic activities, effective rehabilitation, and quality of life of the patient. The prevalence of pain in patients with spinal cord injury is high: in some studies ranging from about 62% to 84% of patients. Back pain is also a feature of other injuries and conditions. For example, postural abnormalities and increased muscle tone in Parkinson's disease may cause back pain, where the prevalence can be as high as 74%. Other conditions associated with back pain include disc rupture, congestive heart failure and osteoarthritis.

Because back pain is often intractable within the current spectrum of clinical modalities, new technology is needed for pain management.

SUMMARY OF THE INVENTION

This application discloses various components of a technological system that can be used for stimulation of the spinal cord for the purpose of treating back pain.

A plurality of electrodes is arrayed on a backing that conforms to the spinal cord. The electrodes can be configured for accommodating movement while stimulating the spinal cord of a subject, as part of a spinal cord stimulation apparatus. The floating electrodes are flexibly mounted to the substrate such that when the electrode array is implanted into the subject, individual electrodes float or move resiliently relative to the substrate to an extent sufficient to accommodate pulsations of the surface of the spinal cord within the dura.

The electrode array can be maintained on the spinal cord at a chosen location by way of a spring or support structure that is anchored to an anatomical structure outside the spinal cord itself, but near the site of implantation in the spine. Suitable anchoring structures include the vertebrae and the dura. Secured in this fashion, the compliant support structure maintains a gentle pressure of the electrode array against the spinal cord so as to stay in electrical contact but minimize the risk of injury or inflammation. The device can accommodate movement of the spinal cord laterally, transversely, and in a caudal-rostral fashion so that the electrode array remains in place.

An aspect of the invention is an implantable device for stimulating the spinal cord of a subject. In general terms, the device has an array of electrodes configured to conform to a region of the spinal cord in the subject such that the electrodes directly contact the spinal cord; and a support structure configured for securing to an anatomical structure outside the spinal cord and configured to urge the array towards the spinal cord so as to maintain contact of the electrodes in the array on the spinal cord. Anatomical structures "outside the spinal cord" are beyond the cord and the dentate ligaments, but preferably within the spine and supporting tissues, and include the vertebrae and the dura of the spinal canal.

The support structure may be configured for securing to the dura. For example, the support structure may have a first flexible member that extends laterally towards and engages the left margin of the dura, and a second flexible member that extends laterally towards and engages the right margin of the dura. Optionally, the first flexible member also engages the left dentate ligament, and the second flexible member engages the right dentate ligament.

Alternatively or in addition, the support structure is configured for securing outside the dura: for example, to any one, two or more than two positions on one or more vertebrae in the subject. Exemplary is a strap bridging the lamina of a single vertebra. The support structure may also have a cuff configured to engage the dura at or near an access site during implantation of the device into the subject, thereby sealing the access site, and one or more electrical leads that pass from the arrayed electrodes through the cuff to provide electrical power from outside the dura for stimulating the spinal cord.

An exemplary device for securing to a vertebra has the following components: (a) an array of electrodes configured to contact the spinal cord; (b) a deformable support structure configured to urge the electrodes of the array into contact with the spinal cord during movement of the spinal cord within the dura; (c) one or more connecting members configured to pass from the support structure out through the dura; and (d) an attachment portion configured for securing the connecting members to a vertebra. The support structure can be configured to maintain pressure of the array upon the spinal cord within a desired range while accommodating changes in position of the array relative to the vertebra that result from movement of the subject in which it is implanted. The deformable support structure is compliant so as to be compressible during implantation, and has a spring action that urges the structure in a direction that is substantially opposite of the direction by which it was compressed. By gently compressing the structure against the spinal cord during implantation, the device will continue to urge the electrode array towards the spinal cord once it is affixed to a vertebra.

The support structure can comprise one or more flexible loops between the array and the connecting member with one or more of the following characteristics in any combination: the loops can be oriented substantially parallel with the spinal cord when the array of electrodes is in contact with the spinal cord; the loops can be oriented at an angle traversing the spinal cord when the array of electrodes is in contact with the spinal cord, thereby being in a position to accommodate both transverse and lateral movement of the spinal cord; the loops can extend horizontally beyond the electrodes on the array; or the loops can constitute or contain one or more electrical leads configured to supply electrical stimulation to the electrodes from a source outside the spinal cord.

The electrodes can be arrayed on a compliant backing that further comprises semi-rigid extensions in rostral and/or caudal directions and/or lateral directions that increase surface area of the backing in contact with the spinal cord. Thus, the electrodes are disposed on a flexible substrate configured to conform to the spinal cord, wherein the array has opposed axial ends along the spinal cord, and wherein the substrate extends sufficiently beyond both opposed axial ends so as to inhibit lifting of any electrodes of the array when the array moves with spinal cord physiological movement within the spinal canal along an axis of the spinal cord. In this configuration, the device may accommodate a total rostral-caudal motion of about 2 cm without lift-off at either end of the backing.

The attachment portion can contain or be configured for securing to a strap, which in turn is secured to lamina of a vertebra of a subject so as to bridge the lamina. The device may also have a cuff skirting around connecting member and configured to be joined with the dura at or near an access site during implantation of the device into the subject, thereby closing the access site; and a scaffold portion attached to the vertical portion between the cuff portion and the spring portion, configured so as to be positioned beneath the access site after the access site is closed.

The connecting members may have one or more electrical leads configured to supply electrical stimulation to the electrodes from a source outside the spinal cord. Such electrical leads can have a first lead portion extending from the attachment portion to the support and a second lead portion extending from the attachment portion to a stimulation signal generator, wherein the first lead portion is coupled to the second lead portion at a connector having a first connector portion mounted to the attachment portion, the first lead portion configured to be more resistant to failure than the second lead portion. There may be an electrical connector at or near the position where the device exits the dura, whereby electrical leads passing from the electrodes through the connecting members to the connector may be electrically and reversibly connected to a power source.

Another aspect of the invention is a strap structured for securing to lamina of a vertebra of a subject so as to bridge the lamina, the strap being configured to receive and support the attachment portion of a device, thereby maintaining pressure of the array of the device upon the spinal cord of a subject in which the device is implanted such that the pressure is maintained within a specified range. An implantable device of this invention and the strap may be manufactured, marketed, or supplied separately or together in kit form.

Another aspect of the invention is an apparatus configured to receive and install an implantable device of the invention in a subject at a position wherefrom pain experienced by the subject can be relieved. The apparatus has a holding member configured to receive and reversibly secure the implantable device while it is being implanted into a subject in need thereof, and a retractable measuring rod configured so that the spring portion or support structure of the device can be positioned and installed at a measured distance away from the spinal cord in the subject such that the array of electrodes is urged upon the spinal cord within a desired or predetermined pressure range. The device and the apparatus can be manufactured, marketed, or supplied separately, or together as a combination.

Another aspect of the invention is a method for implanting a spinal cord stimulation device. The method comprises accessing the spinal cord through a surrounding dura of a spinal canal; positioning the spinal cord at a desired location within the spinal canal; placing an array of electrodes in contact with the spinal cord; coupling a deformable support structure between the array and the dura of the spinal canal so that engagement between the electrodes and the spinal cord remains within a desired range as the spinal cord moves within the spinal canal from the desired location throughout a physiological movement range; and sealing the array and support within the spinal canal.

The device may be secured to a vertebra by creating an incision in the dura over the dorsal aspect of the spinal canal of the subject; positioning the arrayed electrodes over the dorsal spinal cord at a location that is essentially symmetrical between the left and right dorsal root entry zones; lowering the support structure towards the spinal cord so as to compress the spring portion and engage the electrodes with the spinal cord within a desired pressure range; closing the incision around the connecting members; and securing the attachment portion to a vertebra of the subject. This may comprise loading the device on an installing apparatus of this invention, positioning and lowering the device onto the spinal cord by manipulating the apparatus, detaching and removing the apparatus from the device following step (e), and closing the incision around the connecting members once the apparatus has been removed.

The device may be secured to the dura by excising the dura over the dorsal aspect of the spinal canal of the subject; compressing the spring or support structure; positioning the compressed device such that the arrayed electrodes engages a region of the spinal cord that was exposed; allowing the device to expand so that the array is urged towards the spinal cord; and closing the dura.

Another aspect of the invention is a method and a device for use in stimulating a spinal cord by delivering an electrical stimulus to a targeted region of the spinal cord by way of a device according to this invention. The electrical stimulus can comprise a pattern of electrical pulses or signals. The stimulus is applied so as to inhibit sensation of pain by the subject; or to inhibit symptoms of Parkinson's disease, spinal cord injury, or congestive heart failure in the subject.

Further embodiments of the invention will be apparent from the description that follows.

DRAWINGS

Figure 1B:
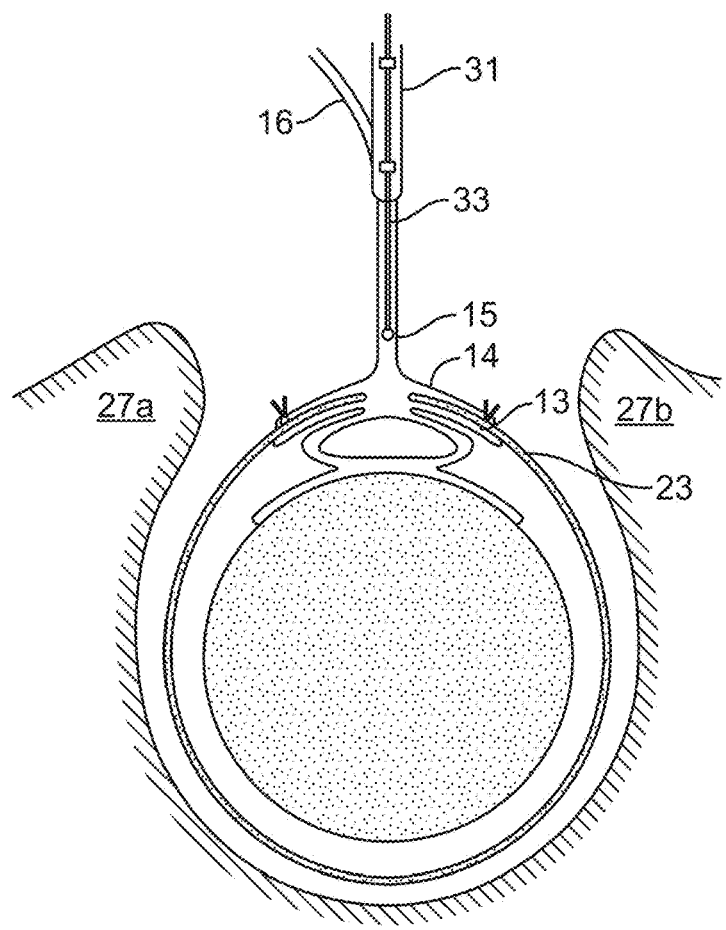
Figure 1C:
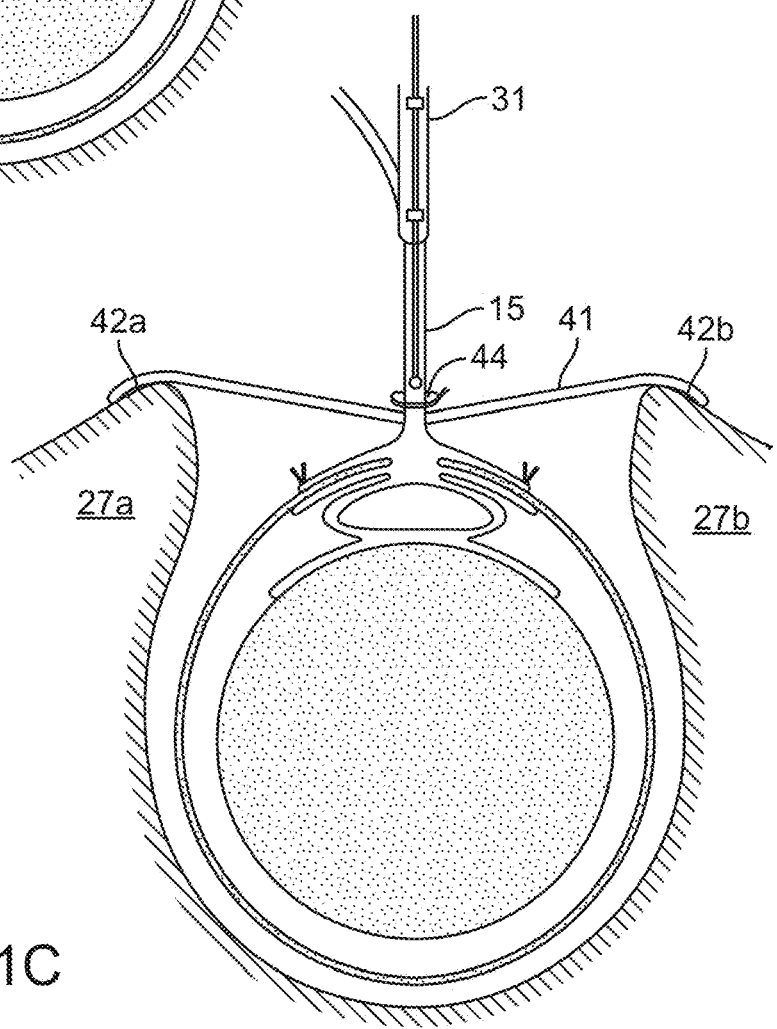
Figure 1D:
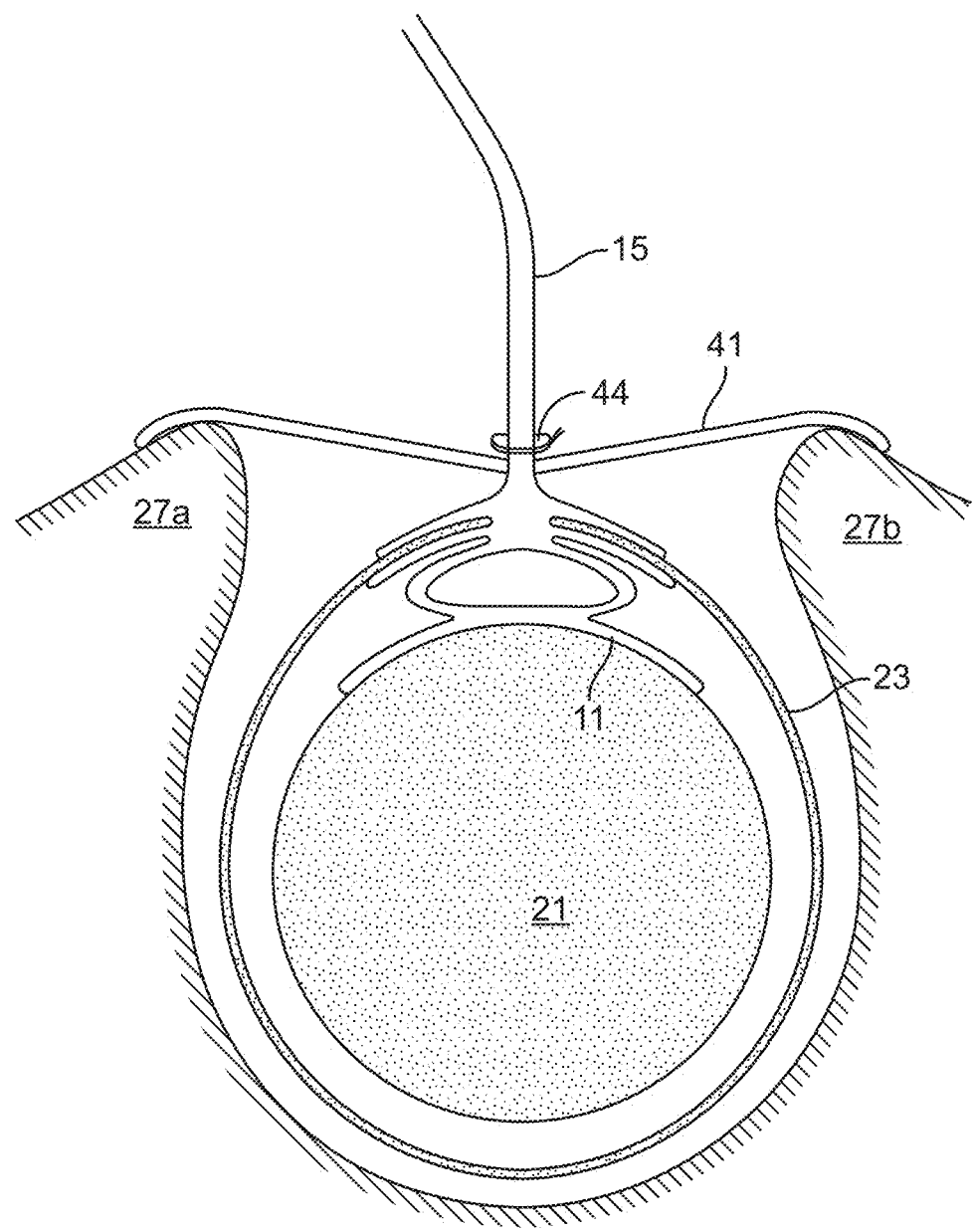

FIG. 1A is a cross-sectional view of a device configured to secure an electrode array to a vertebra. The electrode bearing portion 11 is being positioned on the surface of the spinal cord 21 using a device positioning apparatus (DPA) 31. The dural cuff 14 is secured against the connecting member 15 containing the lead 16. In FIG. 1B, the spacing rod 33 is retracted, and the dura 23 is sutured to the dural cuff 14. In FIG. 1C, the device is secured to a strap 41 which in turn is secured to the vertebral lamina 27a and 27b. FIG. 1D, the device positioning apparatus 31 has been disengaged from the device and removed.

FIGS. 2A to 2D are side (longitudinal) views of the device positioned on the spinal cord and secured to a vertebra. FIGS. 3A to 3D are top-down views of the device positioned on the spinal cord and secured to a vertebra.

FIGS. 4A to 4E are side view illustrations showing a step-wise procedure by which the device may be installed into an operative position on the spinal cord. FIGS. 5A to 5C show the same procedure from a top down view. FIGS. 6A to 6D are magnified lateral views showing details of how the device is positioned to optimize pressure of the electrode bearing portion on the spinal cord.

FIG. 7A shows an oblique view of a prototype device configured for securing to the inner margin of the dura. An electrode bearing portion 11 is configured to conform to a surface of the spinal cord. Upon implantation, extensions 17 of the backing project outwards from the spinal cord toward the support structure 10, where there are pins 18 for engaging the dura. FIG. 7B shows the device in cross-section, after implantation against the spinal cord 21 and being secured to the dura 23. FIG. 7C is a detail showing suturing of the dural cuff 14 to the dura 23. FIG. 7D is a detail showing a securing pin 18 engaged in the inside of the dura 23.

Figure 8A:
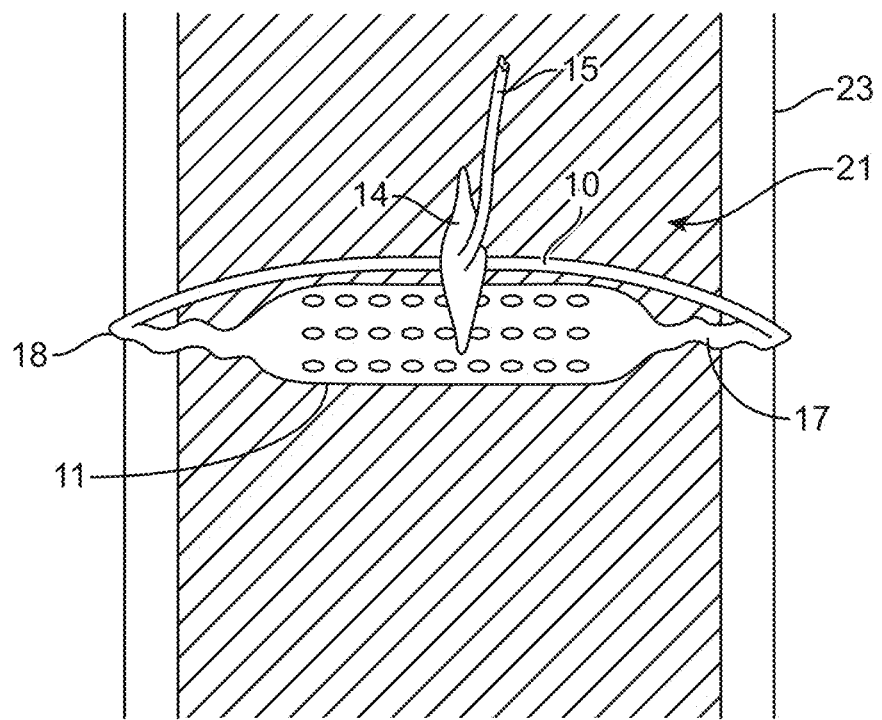
Figure 8B:
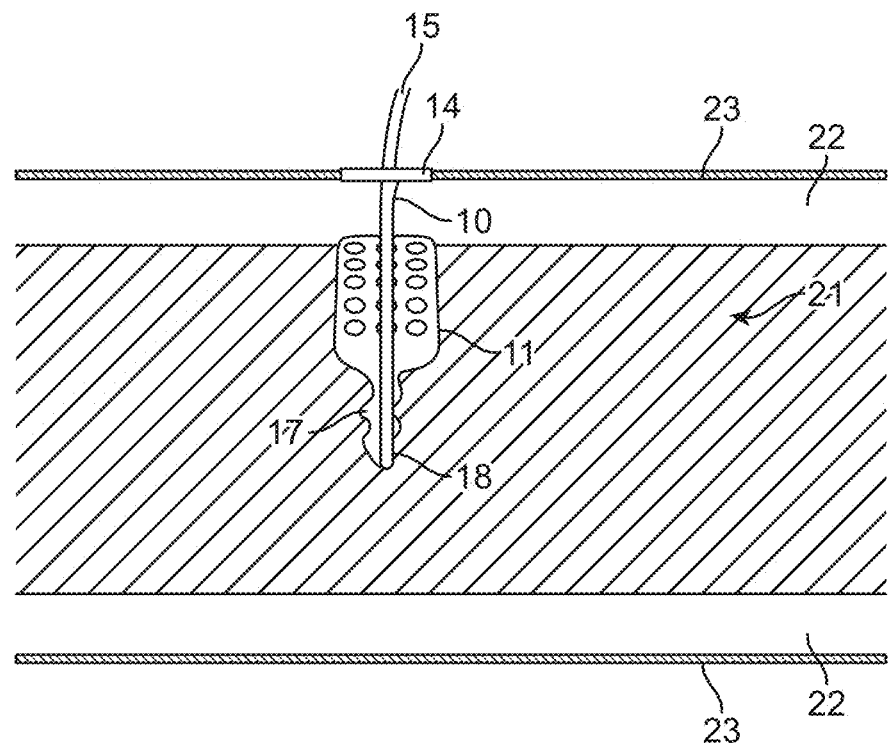

FIG. 8A is a view of the device depicted in FIG. 7A, placed onto the spinal cord, viewed from above the dorsal surface of the spinal cord to which the electrode array has been secured. FIG. 8B is a side view of the device where the spinal cord 21 is shown longitudinally, and the dura 23 has been cut away.

FIGS. 9A, 9B, 9C, and 9D show steps whereby the device may be implanted through a dural incision. The pins 18 on the support structure 10 engage the dura 23, and the electrode bearing portion 11 conforms to the spinal cord 21 so that the electrodes may have direct contact.

Figure 10A:
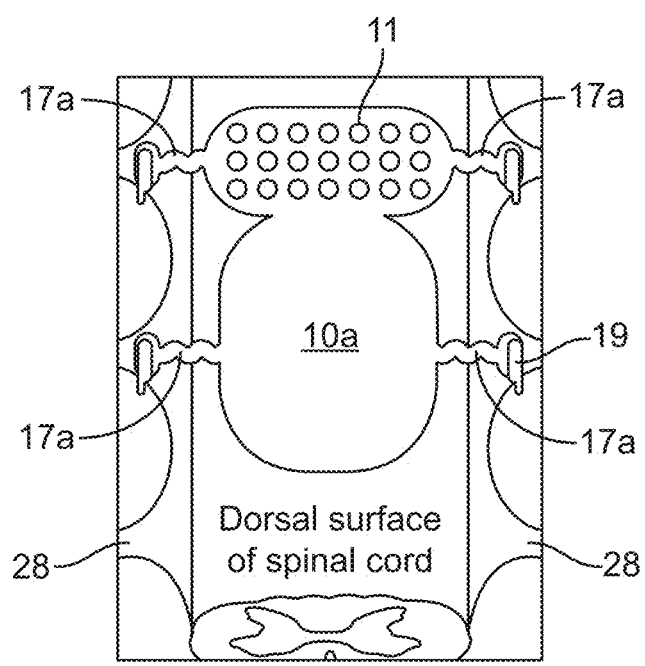
Figure 10B:
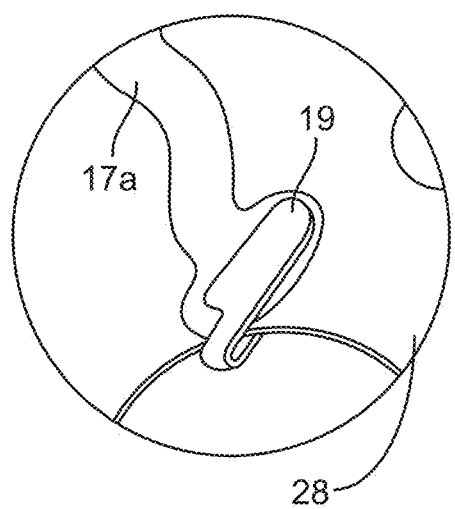

FIG. 10A show an electrode array configured to be clamped to the dentate ligament 28 on each side of the spinal cord. FIG. 10B shows a detail of a clip 19 that affixes an extension 17 of the array to the dentate ligament 28.

Figure 11A:
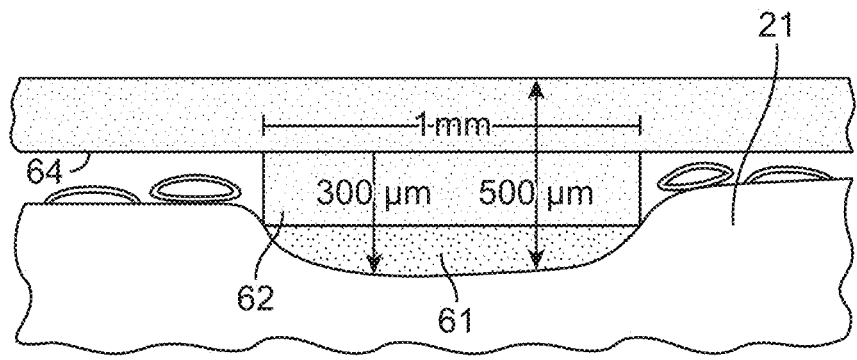
Figure 11B:
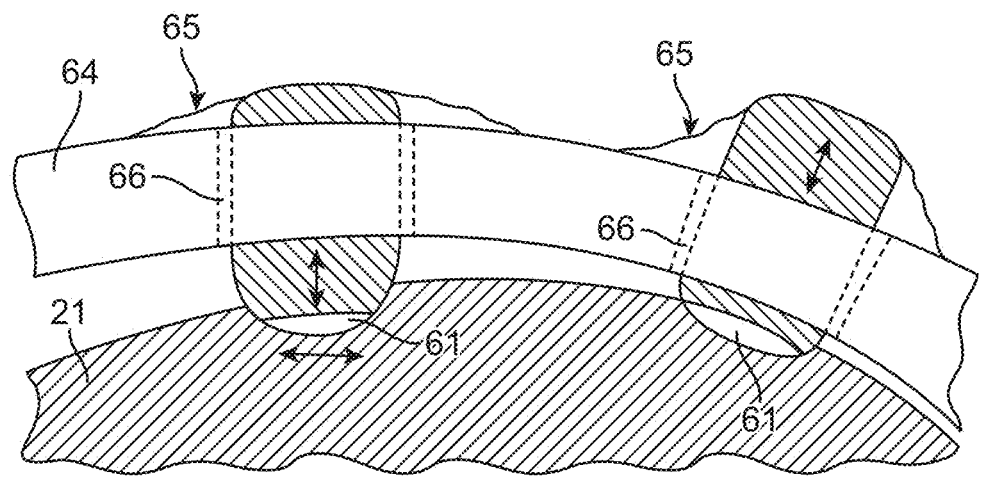

FIG. 11A is a schematic depiction of an electrode in cross-section, extending from the backing upon which it is arrayed. FIG. 11B shows electrodes arrayed in the backing so as to provide a degree of mobility.

Figure 12A:
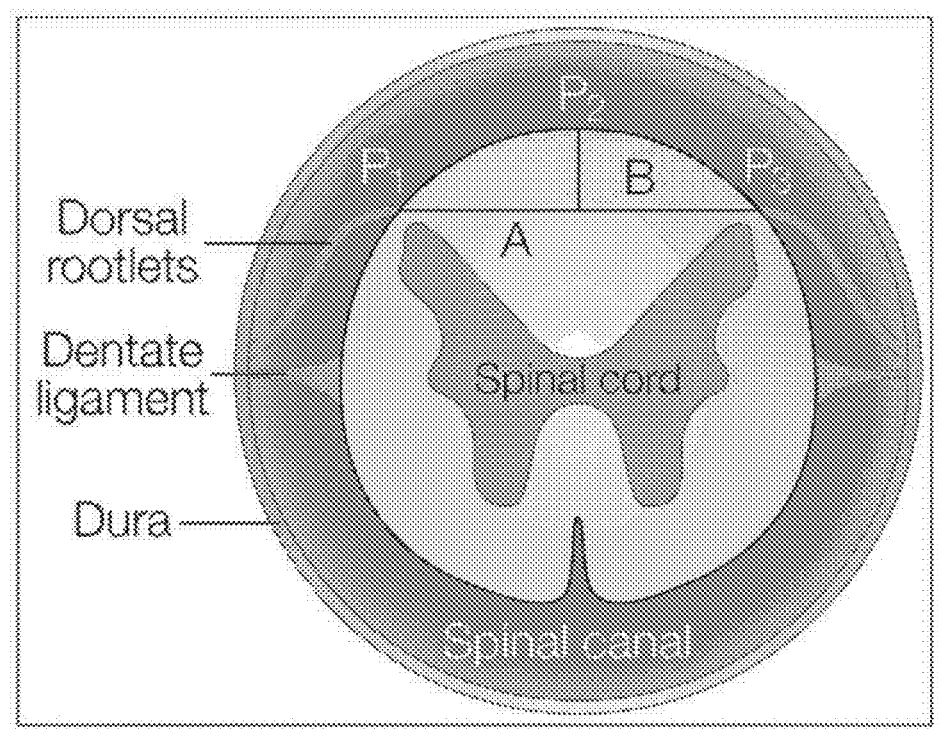
Figure 12B:
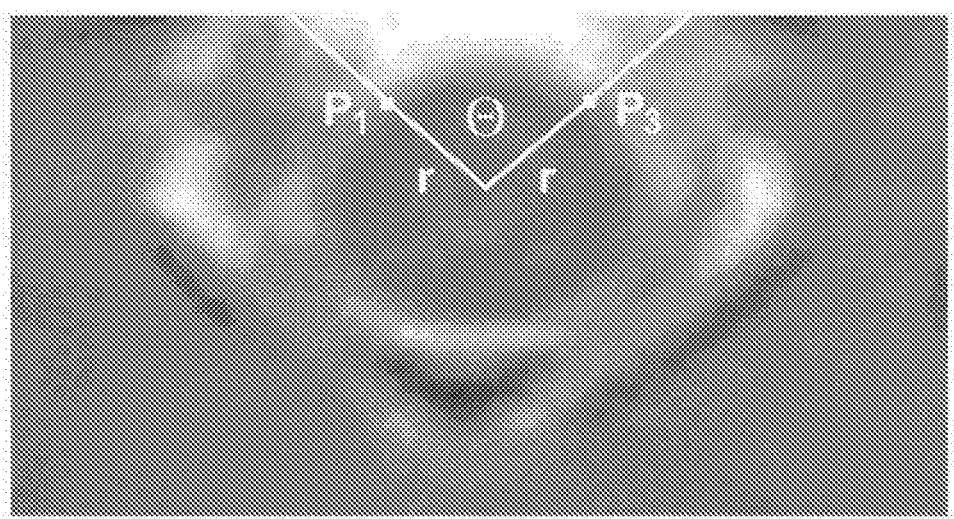
Figure 13A:
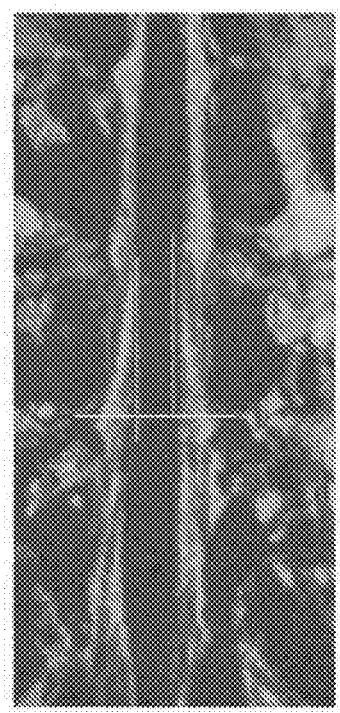
Figure 13B:
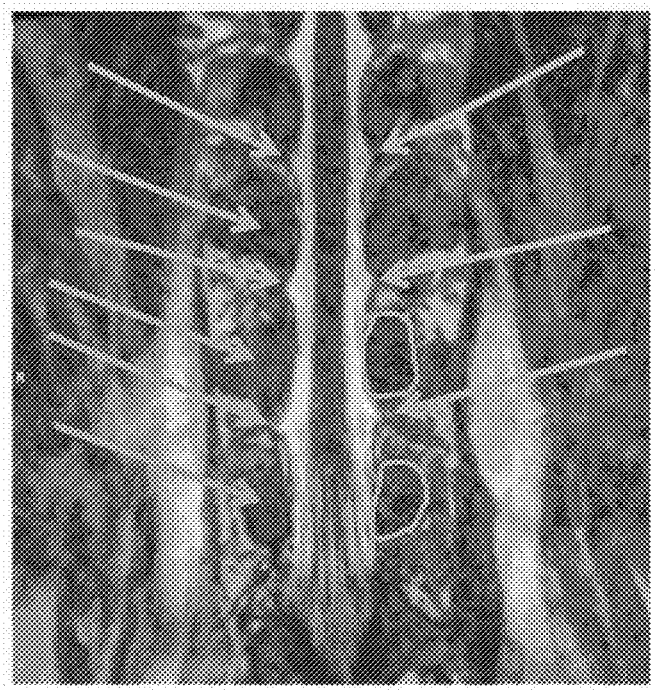

FIGS. 12A and 12B are a drawing and a spinal cord image showing calculation of the arc length between dorsal-root entry zones. FIGS. 13A and 13B are images of a spinal cord showing movement of a spinal cord between neutral and flexed positions. The images can be used to measure spinal cord contraction and expansion along the rostral-caudal axis.

Figure 14:
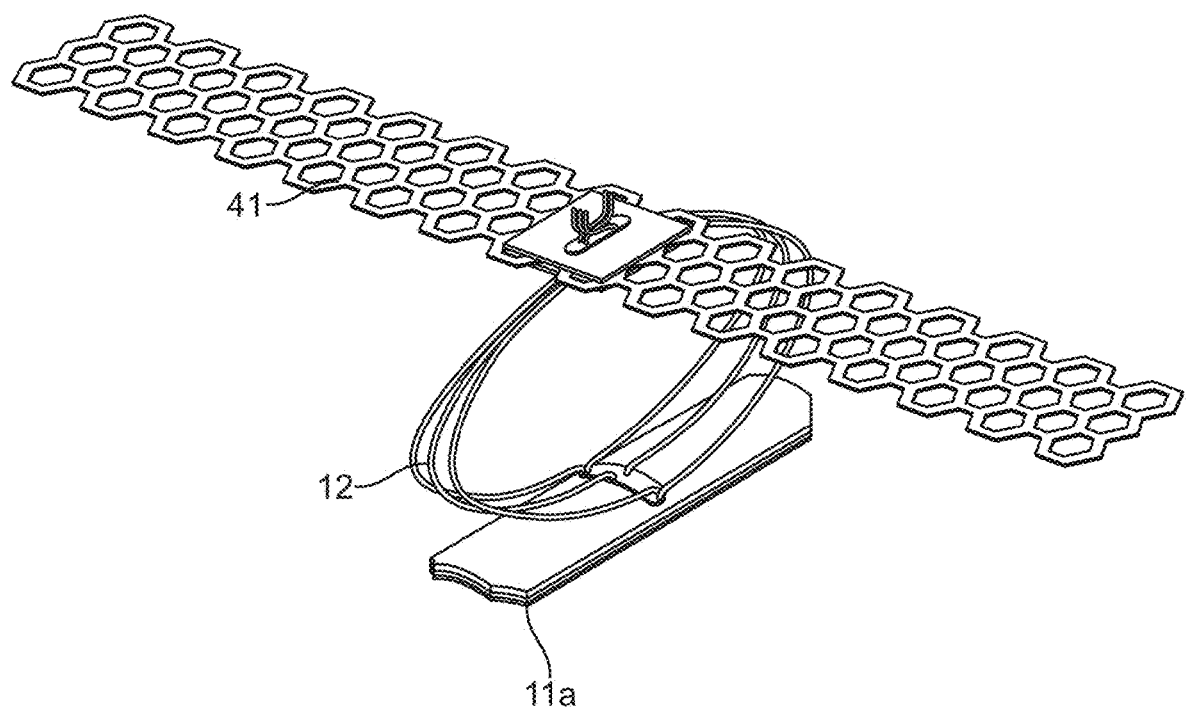

FIG. 14 illustrates a working prototype in which an array backing is secured to a transverse strap by way of a compliant (spring-like) structure in the form of a triple loop (loop area 160 mm$^2$). When mounted on a spinal cord stimulator apparatus, the prototype accommodated a total rostral-caudal motion of 2 cm without lift-off of either end of the backing.

Figure 15:
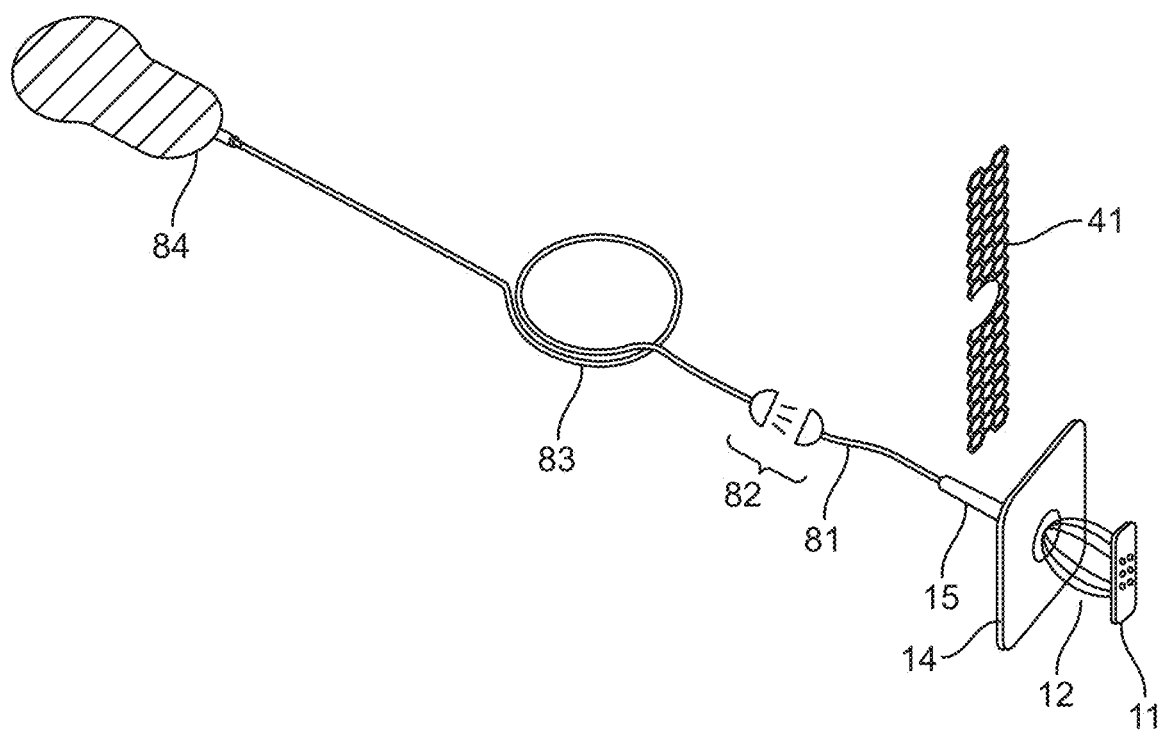

FIG. 15 provides an overall view of a spinal cord stimulation apparatus. Included are an electrode bearing portion 11, a spring portion 12, a strap 41 for securing to a vertebra in the subject, an electrical connector 82, and an external component 84, which is a signal generator that comprises a power source and electronics for controlling the electrical stimuli.

DETAILED DESCRIPTION

One of the factors that limits spinal cord stimulation as an effective treatment of intractable back and leg pain is the inability of the standard devices to selectively modulate the targeted neural fibers. Commercially available devices can inadvertently stimulate neighboring non-targeted structures, such as the dorsal nerve rootlets. This is due to the shunting effects of a layer of highly conductive cerebrospinal fluid located between the epidural electrodes and the spinal cord surface. Shunting of the electrical current produced by the electrode away from the target treatment site limits therapeutic efficacy in up to half of all patients implanted with a standard epidural stimulator. See Eldabe et al., Neuromodulation 13 201-209, 2010.

This invention provides a technology whereby electrode arrays can be more reliably positioned in contact with the spinal cord. Gentle pressure is maintained using a spring or support structure anchored to an anatomical feature or structure outside the spinal cord. Suitable anchor points include anatomical structures at the margins of the spinal canal (particularly the inner wall of the dura), and immediately outside the spinal canal (exemplified by the vertebrae).

FIG. 15 shows an embodiment of the securing system of this invention as part of a spinal cord stimulation apparatus. An electrode bearing portion 11 having an array of electrodes is configured to conform to the spinal cord of a subject (not shown) who is in need of spinal cord stimulation. A spring portion 12 comprising flexible loops is configured to urge the electrode bearing portion 11 against the spinal cord. A dural cuff 14 is configured for joining to the dura, sealing the spring portion 12 within the intradural space. A connecting member 15 (carrying electrical leads connected with electrodes in the electrode bearing portion 11) exits the dura, and is configured for attachment to a strap 41, which is used to secure the device to a vertebra in the subject. A first lead portion 81 has an electrical connector 82 which connects to a second lead portion 83 (a relay lead), which in turn is connected to an external component 84. The first lead portion 81 is generally more resistant to failure than the second lead portion 83, which can be detached at the electrical connector 82 and replaced. The external component 84 comprises a power source and electronics for controlling the electrical stimuli.

The electrode array and support structures of this and related inventions and their various components are being commercially developed under the mark "I-Patch".

Rationale

The neural mechanisms that mediate the clinical effects of SCS are complex and likely involve activation of multiple ascending and descending neural pathways within the spinal cord. In general, electrical stimulation will evoke sensory perceptions in the painful area of the body in order for the treatment to be effective. To accomplish this, the region within the dorsal column of the spinal cord that contains axons that are functionally related to the painful body area must be activated. Dorsal column axons are somatotopically organized, meaning that the axons that are functionally related to a particular body area are positioned in close proximity to each other, and there is an orderly anatomical pattern of organization within the spinal cord for the different groups of axons linked to different body areas. In the cervical spinal cord, for example, dorsal column axons functionally linked to the back region may be relatively close to the midline of the spinal cord, and axons linked to the arms are positioned relatively more laterally.

The spinal cord is axially cylindrical, and positioned centrally within the spinal canal. The spinal canal is lined by a dural membrane and contains cerebrospinal fluid (CSF) that surrounds the spinal cord and fills the region between the outside surface of the spinal cord and the inside surface of the dural membrane. This CSF-filled space plays a critical role in normal spinal cord biomechanics and is an important factor that should be considered when performing spinal surgery. During normal movements, such as flexion and extension of the body, the spinal cord moves within the spinal canal, altering its position relative to the dural lining of the spinal canal. The volume of CSF surrounding the spinal cord serves as a frictionless buffer during these movements. In some pathological conditions (e.g. tethered cord syndrome) this normal motion of the spinal cord is impeded by tissue attachments bridging the space between the spinal cord and the dural lining, resulting in dysfunction of the spinal cord. In other pathological conditions, a tissue barrier forms within the spinal canal (e.g. following trauma or infection) that disrupts the normal flow of CSF over the surface of the spinal cord. In these settings, CSF may accumulate within the substance of the spinal cord to form a syrinx and cause neurological dysfunction.

The technology in this disclosure addresses deficiencies of previously available SCS devices by incorporating at least some of the following design features:

- the electrical stimuli are delivered directly to the spinal cord;
- a dense array of electrode contacts enables delivery of highly localized, spatio-temporally synchronized and positionally selective electrical stimuli to any targeted sub-region of the spinal cord;
- the device does not mechanically tether or form a physical connection between the spinal cord and dura that significantly alters the natural support and flexibility provided by the dentate ligaments;
- the implantable electrode assembly has an ultra-thin physical profile that does not obstruct or alter CSF flow patterns around the spinal cord;
- the contact forces between the device and the spinal cord are stable and unvarying, and hence patient movement does not affect these contact properties, which results in optimal electrical coupling between electrode contacts and spinal cord tissue;
- the surgical procedure used to implant the device is well established and safe, and does not substantially increase the risk of complications; and
- the manufacturing cost of the devices provided in this disclosure may be less than that for previously existing devices.

Securing the Electrode Array to the Vertebrae

FIGS. 1A to 3D illustrate an example of the invention in which an electrode array is secured to a vertebra of the subject. FIGS. 1A to 1D are a cross sectional views. FIGS. 2A to 2D are side (longitudinal) views. FIGS. 3A to 3D are top-down views.

Referring to FIG. 1A, the spinal cord 21 in the spinal canal 22 is surrounded by the dura 23. Dorsal rootlets 24 carry sensory (afferent) fibers to the spinal cord. Dentate ligaments (not shown) suspend the spinal cord within the spinal canal. This is surrounded by a vertebra 26 that been opened at the back (top) through which the surgeon may access the spinal cord.

The device comprises an electrode bearing portion 11 bearing an array of electrodes for contacting and conforming to the spinal cord 21, from which to deliver an electrical stimulus. The device further comprises a deformable spring portion 12 in the form of a loop, which acts as a support structure, urging the electrode bearing portion 11 into contact with the spinal cord 21 so as to accommodate movement of the spinal cord within the spinal canal 22.

Referring to FIG. 1B, upon implantation into a patient, the electrode bearing portion 11 is placed on and conforms to the surface of the spinal cord 21. The electrode bearing portion 11 is kept in place by way of the spring portion 12 that presses the array against the cord. Here, the spring portion 12 is depicted as a transverse loop. Alternatively, the loop runs longitudinally along the spinal cord or diagonally to accommodate movement of the spinal cord in a caudal-rostral fashion through the vertebrae. Over top of the spring portion 12 is an attachment arm or scaffold 13, above which is a dural cuff 14 for suturing to the dura 23 during closure. A connecting member 15 containing electrical leads 16 passes up through the dural cuff 14 to an external power source (not shown) that provides a pattern of electrical pulses for stimulating the spinal cord.

Referring to FIG. 1C, following closure of the dura, the strap 41 is placed with lower surfaces 42a and 42b in contact with the vertebral lamina 27a and 27b, where it may be permanently affixed by way of surgical screws (not shown, see FIGS. 3C and 3D below) or other attachment means (not shown). The vertical connecting member 15 of the support device passes through and is secured to an opening 44 near the midpoint of the strap 41 between the two vertebral lamina 27a and 27b. The device may also comprise an attachment means (not shown) by which the connecting member 15 is secured to the strap 41 at a set distance from the spinal cord 21 so as to maintain pressure of the electrode bearing portion 11 against the spinal cord 21 within a desirable range of pressure. The electrode bearing portion 11 thereby maintains a position wherefrom to stimulate the spinal cord 21 without losing contact should the spinal cord move from its neutral position, without injuring the spinal cord and surrounding tissues, and without provoking an inflammatory response.

FIGS. 1A to 1C also show a micromanipulator that is used as a device positioning apparatus (DPA) 31. The surgeon may use the DPA to install the device into a subject at a target site on the spinal cord. The DPA comprises a holding member or handle 32 configured to receive and reversibly secure the implantable device while it is being implanted, and a measuring portion or spacing rod 33 with a lower surface 34 configured to be placed upon the dorsal surface of the spinal cord 21 during the procedure. The DPA is used to position the spring portion or support structure 12 of the device at a measured distance away from the spinal cord 21 such that the electrode bearing portion 11 is urged against the spinal cord 21 within a desired pressure range.

The spacing rod 33 is used to calibrate the distance for lowering the electrode bearing portion 11 onto the spinal cord 21. The spacing rod 33 may be permanently attached to the DPA, or may be retractable. As shown in FIG. 1A, the spacing rod 33 passes through brackets 35a and 35b so that the spacing rod 33 can be lowered to a measuring position, and then raised by way of a handle 36 to a retracted position. The device may be detachably secured to the DPA, for example, using a clamping arrangement or fungible connecting means such as a thin band or suture. The DPA is operated to release the device once the device is secured at the target location on the spinal cord, and then removed from the field. In FIG. 1D, the device positioning apparatus 31 has been disengaged from the device and removed.

Figure 2A:
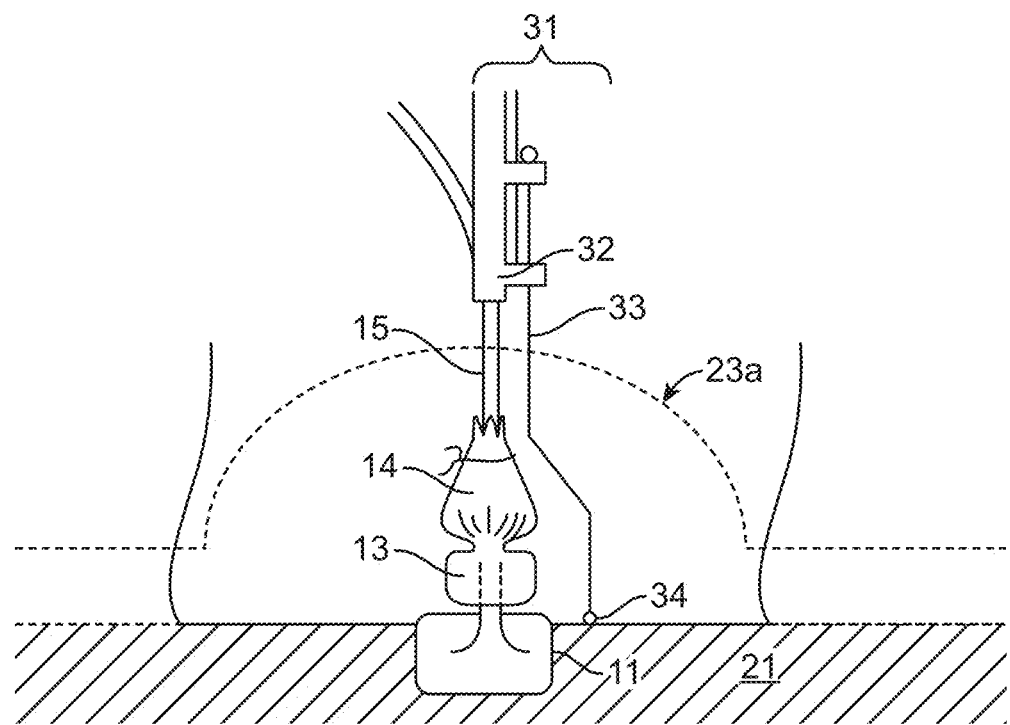
Figure 2B:
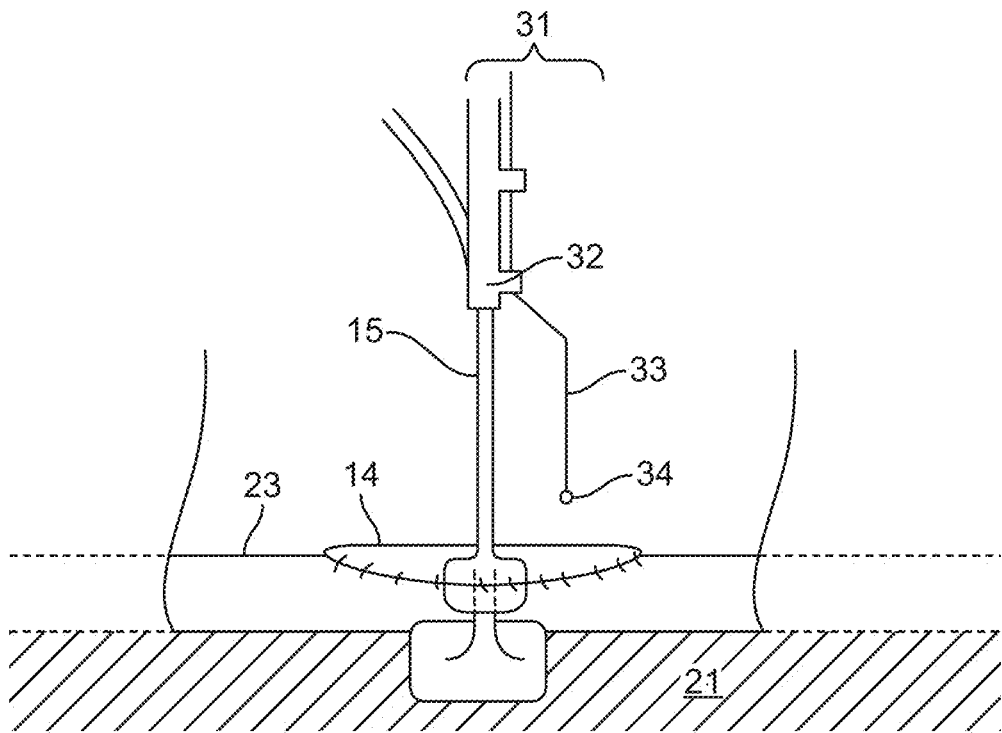
Figure 2C:
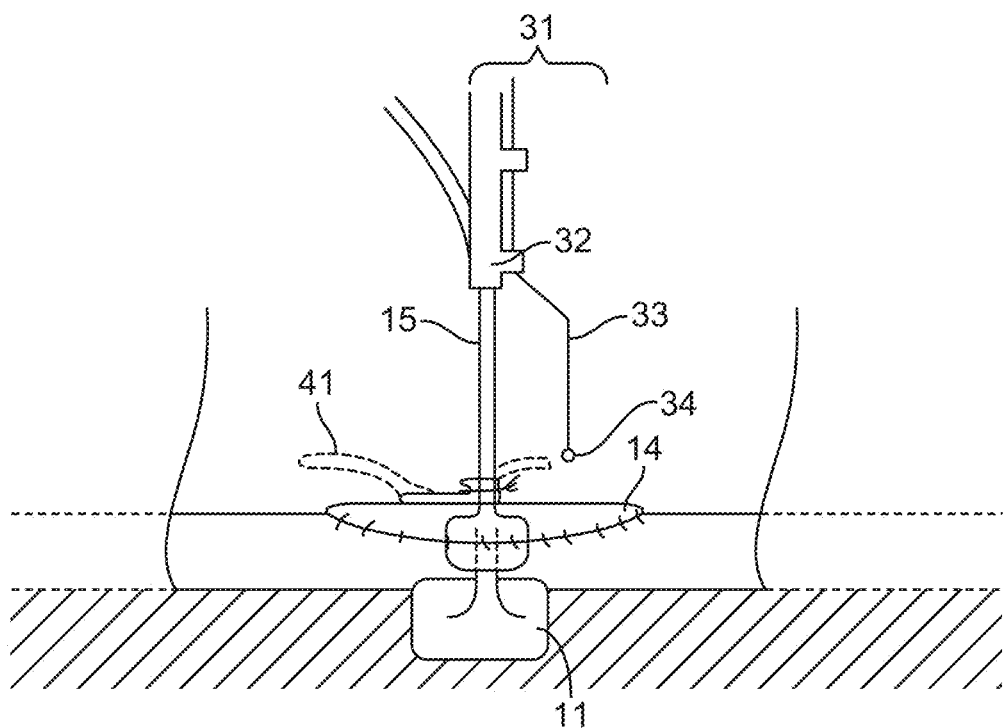
Figure 2D:
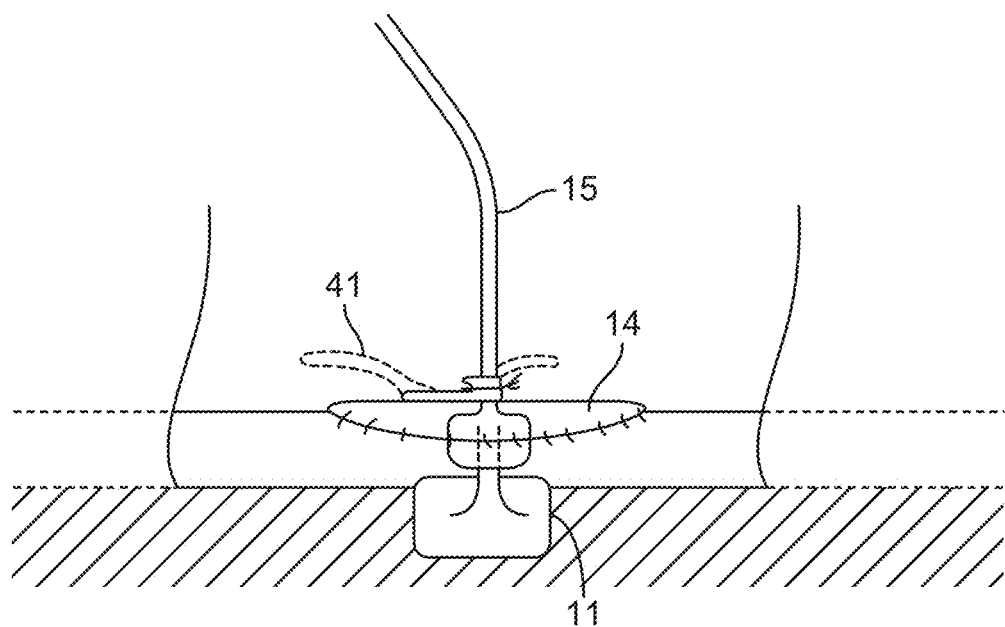

FIG. 2A is a side view showing the reflected edge 23a of the dura as a dashed line. The electrode bearing portion 11 is shown during initial positioning on the spinal cord 21 with the dural cuff 14 secured against the connecting member 15 above the scaffold 13. The spacing rod 33 of the positioning apparatus 31 is in the down position in contact with the spinal cord 21. In FIG. 2B, the spacing rod 33 is moved to the up position, and the dural cuff 14 is secured by suturing to the dura 23. In FIG. 2C, the titanium strap 41 is secured to the vertebral lamina (not shown), and the vertical connecting member 15 is secured to the strap 41. In FIG. 2D, the device positioning apparatus 31 has been disengaged and removed.

Figure 3A:
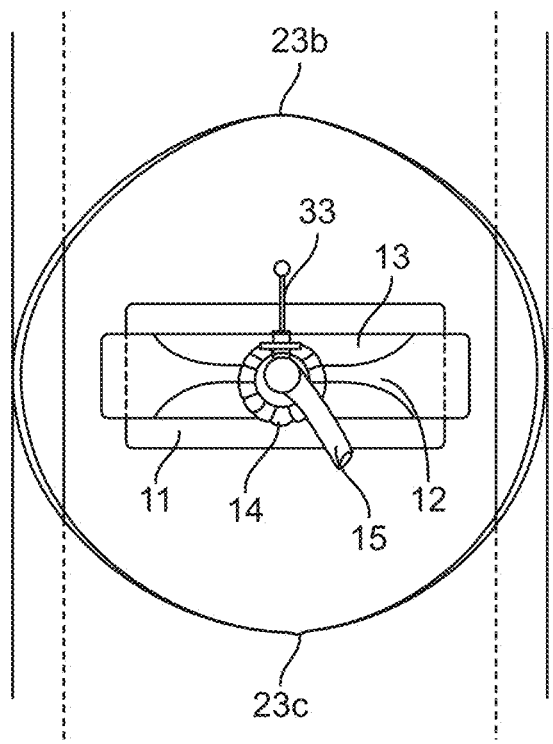
Figure 3B:
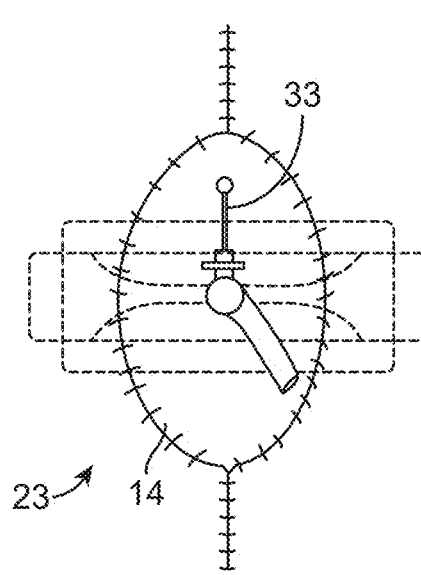
Figure 3C:
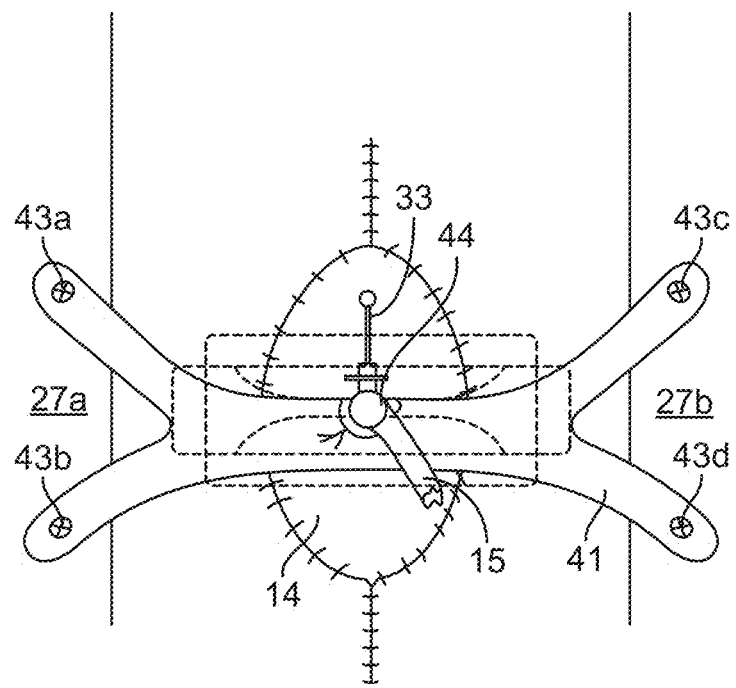
Figure 3D:
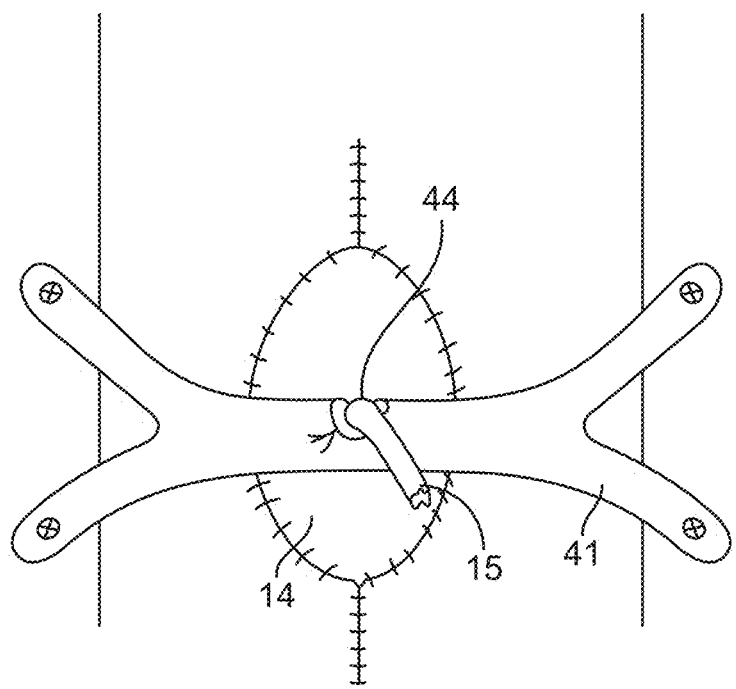

FIG. 3A is a top-down view showing the rostral 23b and caudal 23c limit of the durotomy, with the electrode bearing portion 11, the loop-shaped spring portion 12, the scaffold 13, and the dural cuff 14, with the dural cuff secured against the vertical connecting member 15 before implanting. The spacing rod 33 of the positioning apparatus is in the down position. FIG. 3B shows the dural cuff 14 detached from the vertical connecting member 15 and sutured to the dura 23, with the spacing rod 33 moved to the up position. FIG. 3C shows the vertical connecting member 15 of the device secured to an opening 44 at around the horizontal midpoint of the strap 41, which in turn is secured to the lamina 27a and 27b by way of four surgical screws 43a, 43b, 43c, 43d. In this illustration, the strap bifurcates on each side as it approaches the lamina. In FIG. 3D, the device positioning apparatus has been disengaged and removed.

Components of the Device

In more general terms, a spinal cord stimulating device of this invention may include any of the following features in any operative combination.

For securing to a vertebra, the device comprises an electrode array (as described in more detail below), and a spring portion or support structure that maintains contact of the electrodes in the array with the spinal cord. The spring portion or element is configured (by a choice of shape, thickness, rigidity, and distance away from the array itself) to exert a pressure by the array on the spinal cord within a predetermined or desired range upon implantation of the device into a subject. The range of this pressure might be 0.1 mm Hg through 25 mm Hg. Various mechanical spring shapes are suitable for this compliant element. One such shape is one or more flexible loops that is attached to the upper structure of the device on one side and to the array on another side. For economy of design and operation, the spring portion consists of or contains the electrical leads supplying stimulation to the electrodes.

The support structure may integrally comprise an attachment portion for securing directly to a vertebra. Alternatively, it may comprise one or more vertical connecting members configured for securing to a separate strap that bridges the lamina. The strap may have any suitable shape that spans between and secures to the lamina or other parts of the vertebra within a suitably confined volume. The strap may be packaged or provided together with other components of the device in kit form, or supplied separately.

Other possible components include a cuff portion attached to the vertical connecting member and configured to be joined with the dura at or near an access site during implantation of the device into the subject, thereby closing the spinal canal. A scaffold portion may be attached to the vertical portion between the cuff portion and the spring portion, configured so as to be positioned beneath the access site after closure. There may also be an electrical connector at or near the position where the device exits the dura, whereby electrical leads passing from the electrodes through the vertical member(s) to the connector may be electrically and reversibly connected to a power source.

Alternatively or in addition to the securing apparatus described above, the electrode array may also be provided with attachment arms that wrap at least part way around the spinal cord. For example, flexible attachment arms may extend from either side of the electrode array, with the attachment arms typically being formed at least in part of the substrate or backing material on which circuit components are mounted or formed. Further information about various wrap-around configurations is provided in U.S. Pat. No. 9,364,660.

Apparatus for Positioning the Electrode Support Device During Installation

As explained above in reference to FIGS. 1A to 1C, the device positioning apparatus (DPA) 31 assists the surgeon in placing the support structure with the electrode bearing portion precisely onto the target site on the spinal cord. The DPA is configured to receive and install the device in such a manner that the electrode array abuts and is urged against the dorsal surface of the spinal cord, and is anchored to a nearby vertebra. The DPA comprises a holding member configured to receive and reversibly secure the implantable device while it is being implanted, and a spacing rod 33 configured so that the spring portion 12 or support structure of the device can be positioned and installed at a measured distance away from the spinal cord 21 in the subject such that the electrode bearing portion 11 is urged upon the spinal cord within a desired pressure range.

The DPA can be configured as a rod-shaped hand held device. During surgery, the device is connected to a malleable attachment arm (e.g. modified Greenberg) outside of the surgical cavity. The neurosurgeon grasps and positions the DPA using her left hand. The device assembly is reversibly attached to the end of the DPA. A heavy-gauge suture is run through eyelets on the DPA and looped around the exiting lead of the device. During the insertion procedure the suture is under sufficient tension (the sutures are secured to anchor points on the distal handle of the DPA) to grasp the lead securely. At the appropriate point in the procedure, the suture is cut using microscissors to achieve a smooth and technically simple mechanical release of the device lead from the DPA.

The portion of the DPA rod close to the spinal cord has an acute angle. This angle serves to off-set the point of attachment between the DPA and the device lead several centimeters away from the shaft of the DPA. This design feature serves two purposes: 1) it provides a clearly line-of-sight field of view for the neurosurgeon than would be the case with a straight DPA, and 2) it gives the neurosurgeon the physical access to suture a majority of the device dural cuff circumference to the spinal dura while the device is being held in the optimal position by the DPA. After the device is secured by way of the strap to the lamina of the vertebra, it may not be technically feasible to surgically access much of the circumference of the dural patch. All but a small portion of the dural cuff circumference is sutured closed before the strap is placed, and the portion that remains to be sutured is well away from the strap (i.e. a small portion of the cuff located on the side of the durotomy opening opposite to the strap).

Figure 4A:
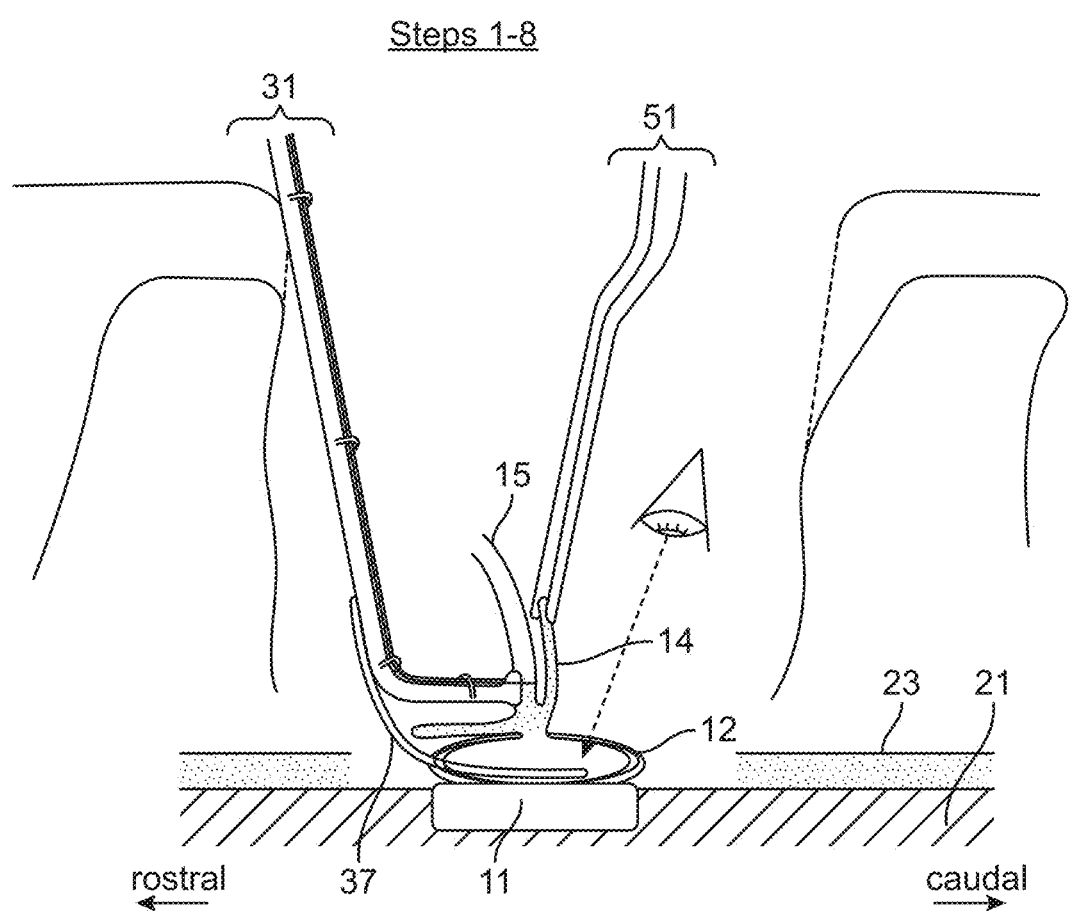
Figure 4B:
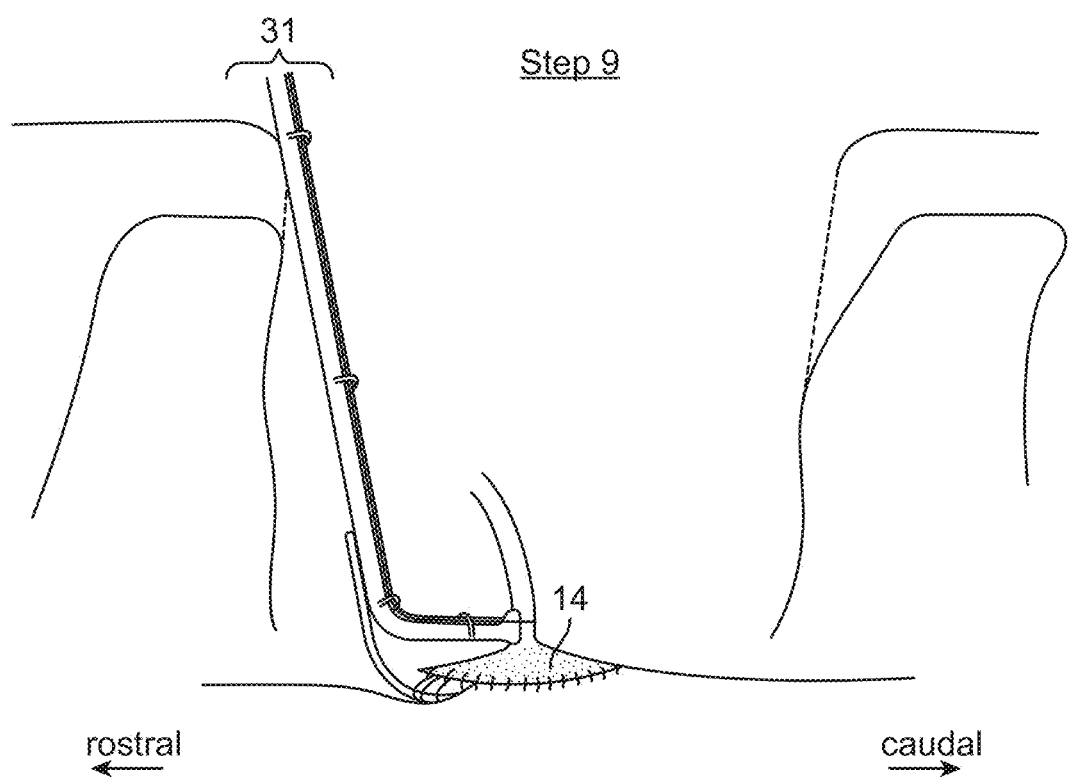
Figure 4C:
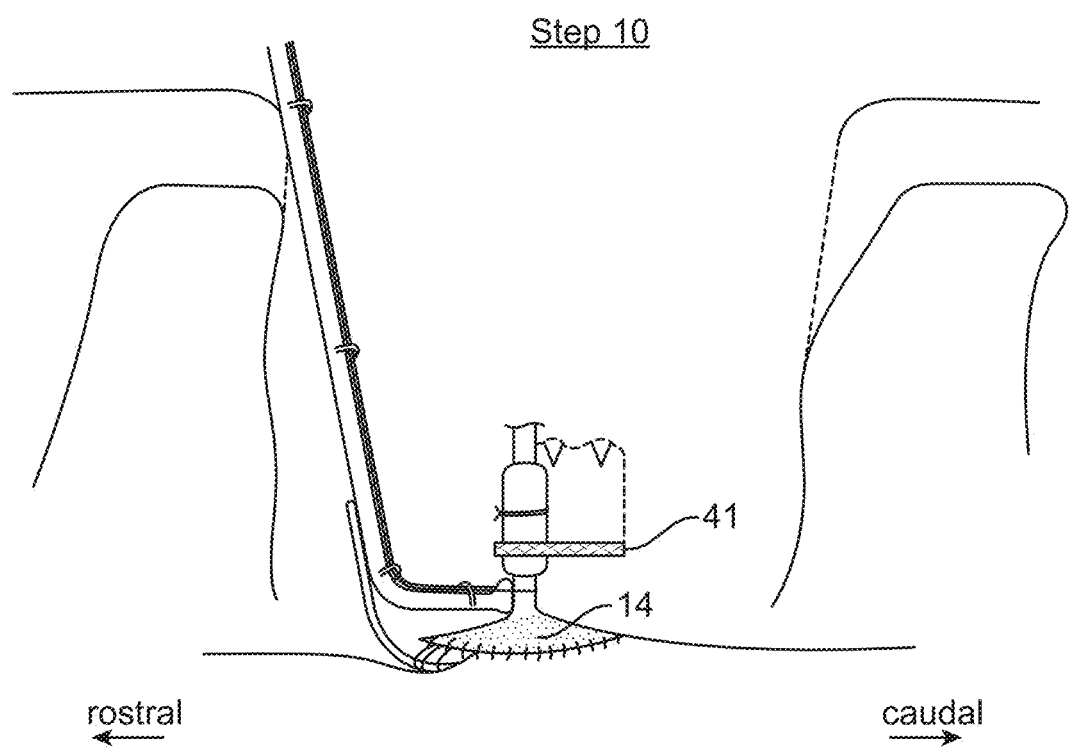
Figure 4D:
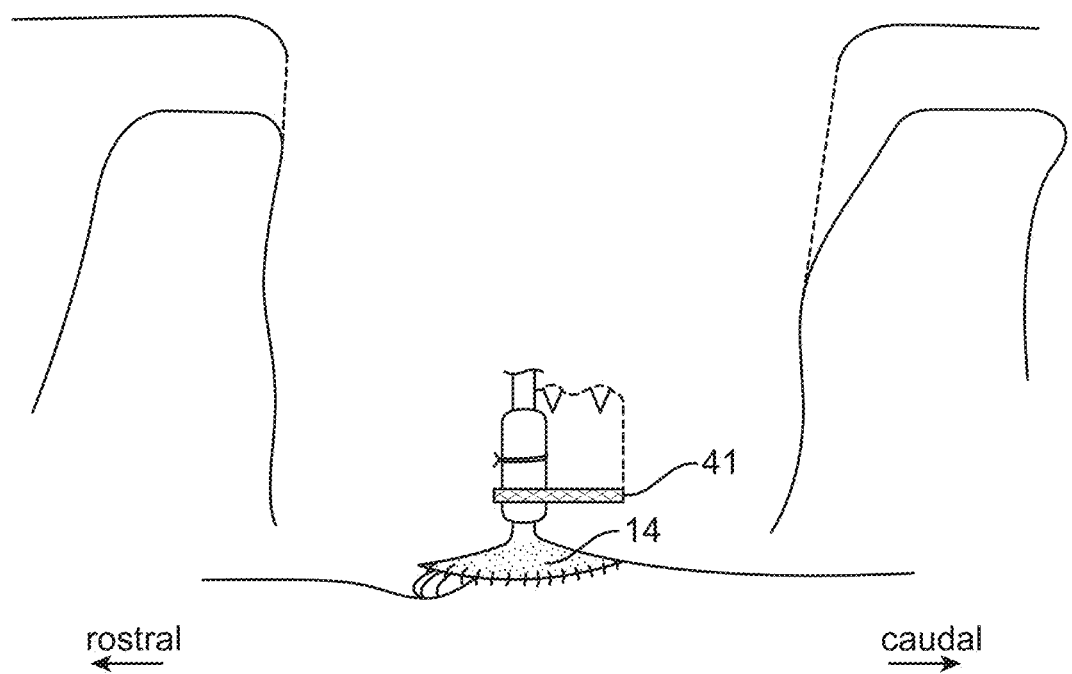
Figure 4E:
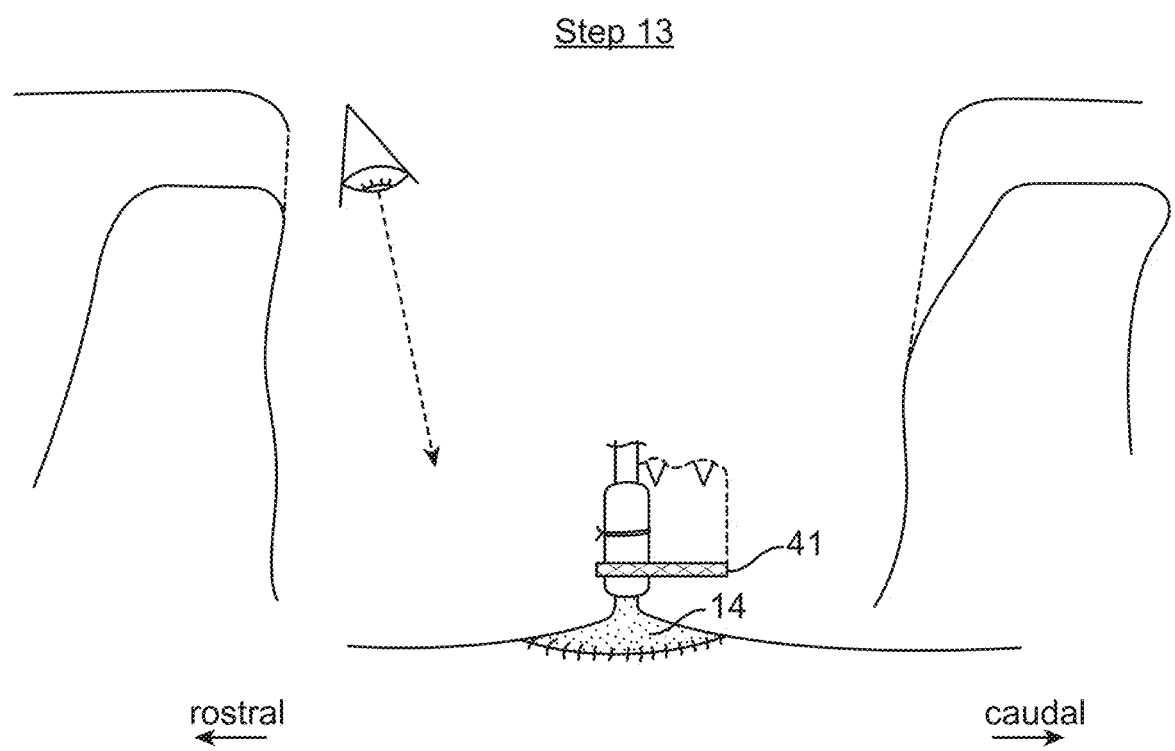
Figure 5A:
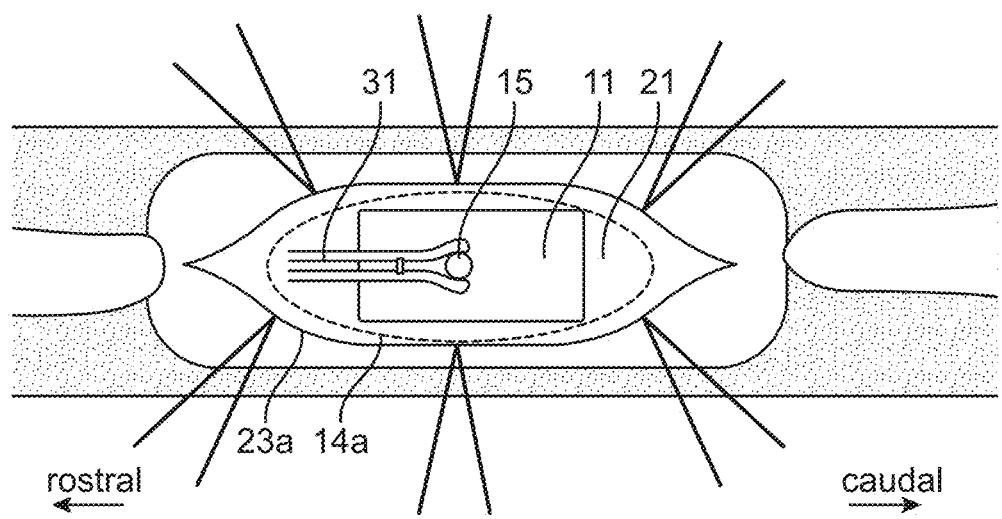
Figure 5B:
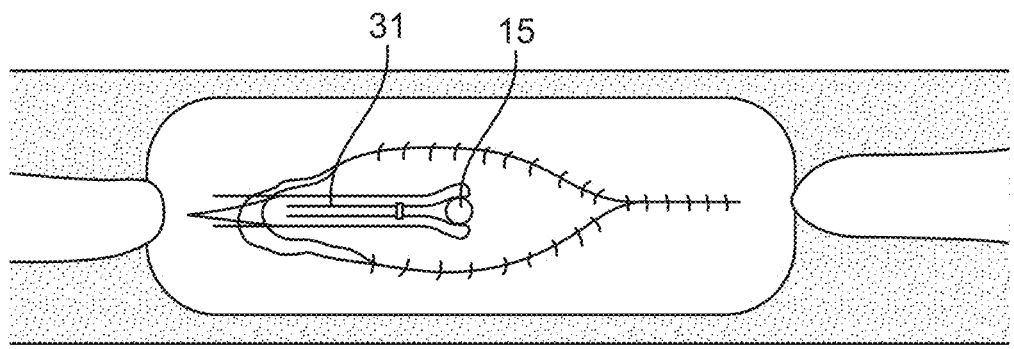
Figure 5C:
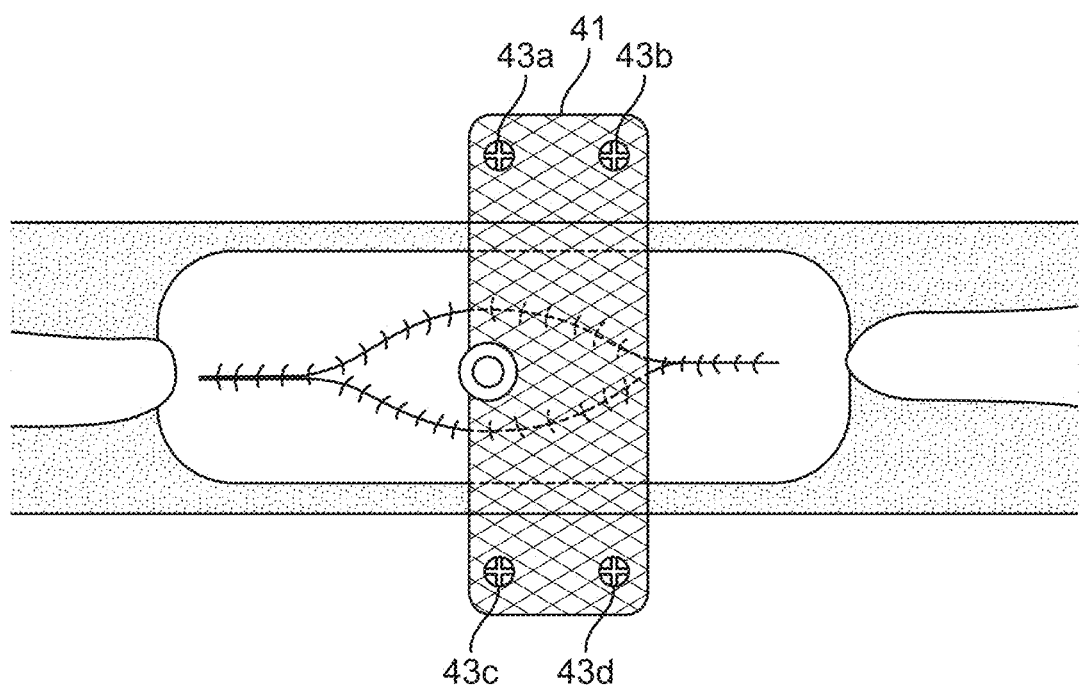
Figure 6A:
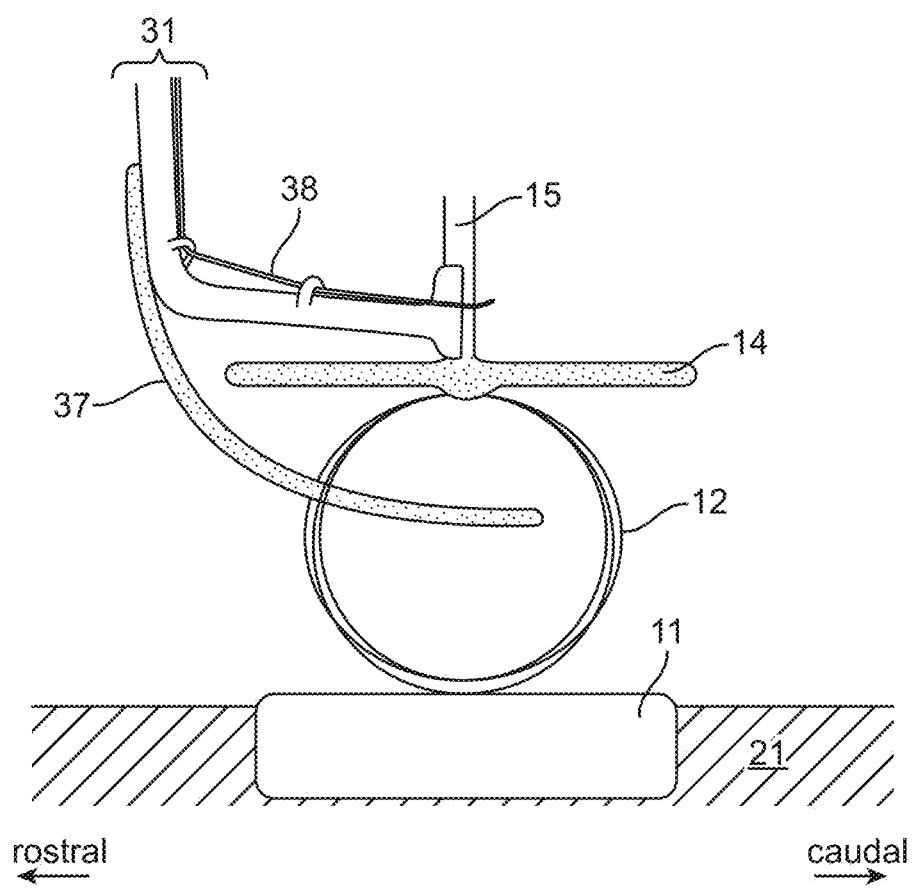
Figure 6B:
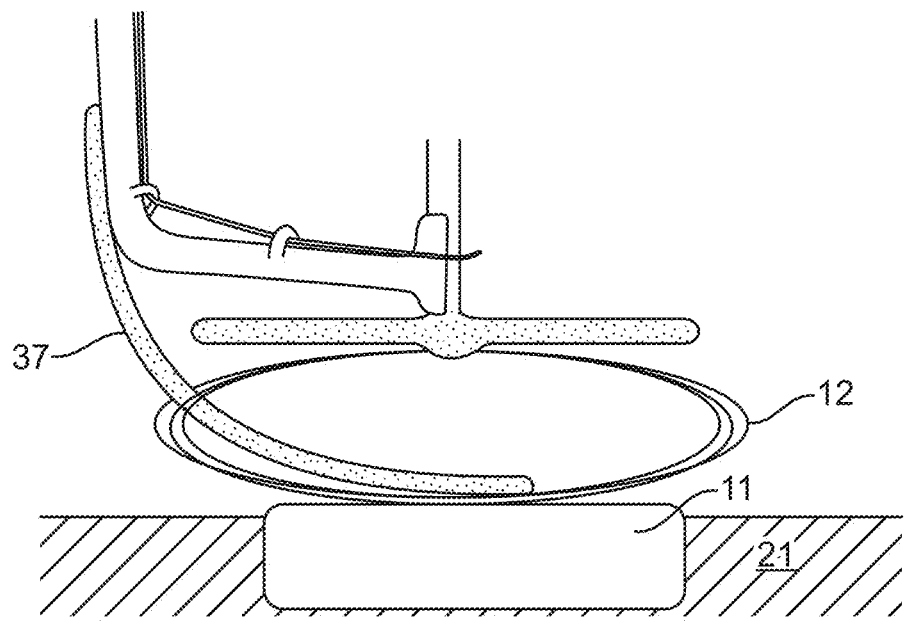
Figure 6C:
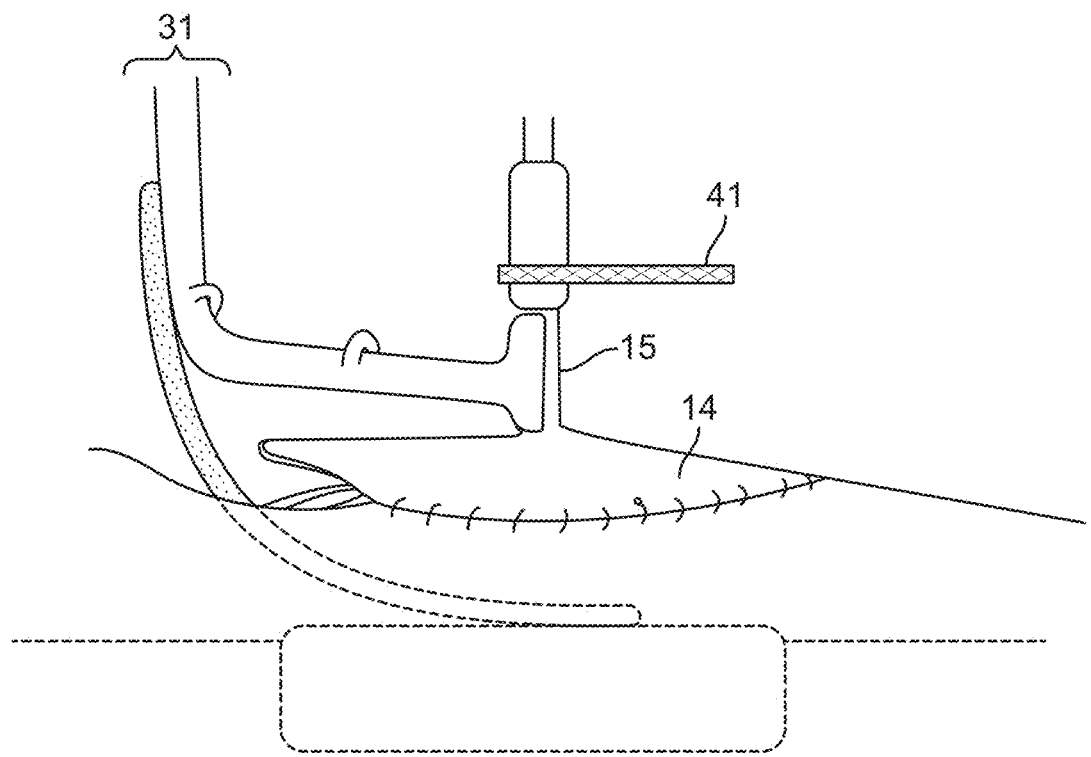
Figure 6D:
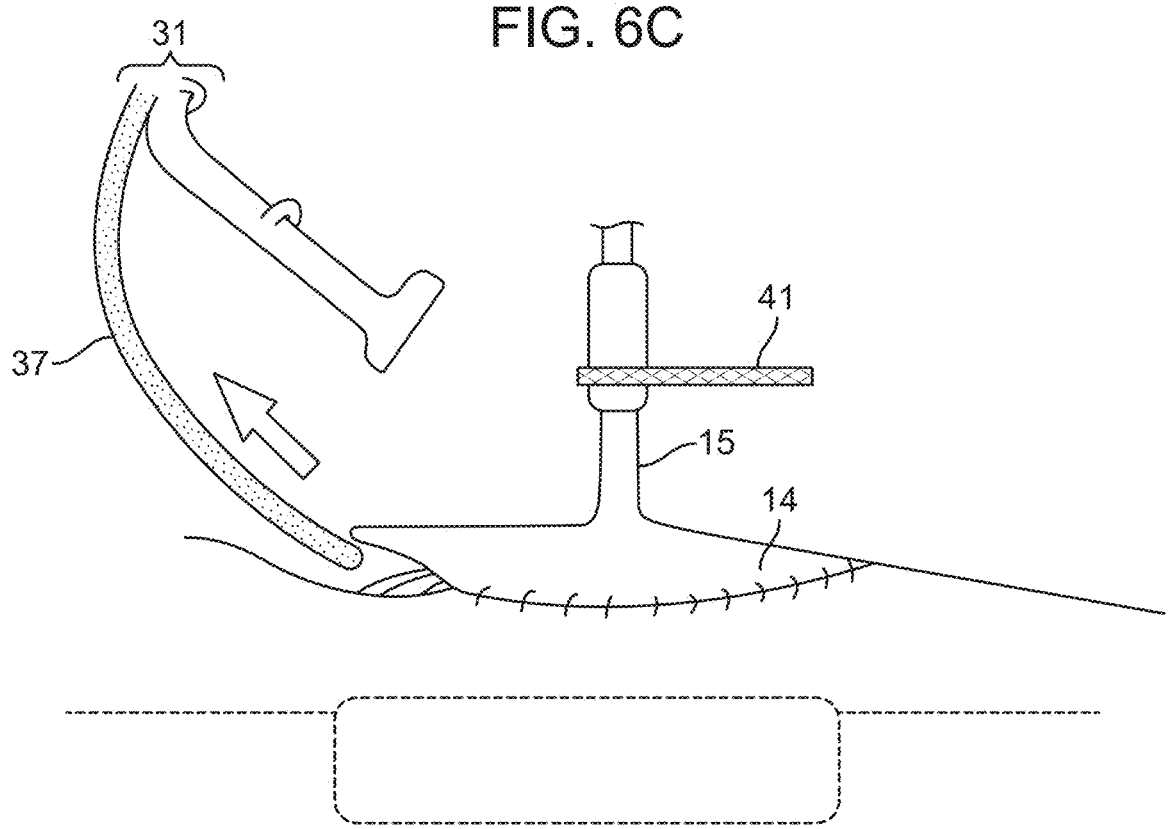

As illustrated in FIG. 4A, the DPA 31 may also be provided with an affixed or retractable distance measurement extension (DME) 37 or measuring rod. The purpose of the DME is to provide the neurosurgeon with visual feedback to set the appropriate distance between the electrode bearing portion of the device and the point at which the lead bundle penetrates the dural cuff during the device implantation procedure. The DME may be gently curved, extending below and parallel to the distal portion of the DPA (the end of which is attached to the device lead). The neurosurgeon is able to visualize the tip of the DME and lowers the device assembly onto the spinal cord, compressing the intradural leads until the tip of the DME just comes into contact with the electrode bearing portion of the device. The midline position of the DME does not interfere with the first portion of the subsequent dural cuff closure step, or damage the intradural leads. Once the device is permanently secured to the strap and it is necessary to disengage and remove the DPA, the curved profile of the DME allows it to be safely removed from the intradural space with a simple rotational and upward movement of the DPA.

Procedure for Installation

General guidance for the surgeon in placing the device onto the spinal cord is as follows. The surgeon should have clear line-of-sight visualization of the electrode bearing portion of the device as it is positioned on the surface of the spinal cord. The distance between the electrode bearing portion of the device and the point at which the leads fuse into the dural cuff exit site can be set precisely during the operation. This sets the tension of the malleable intradural leads at the optimal force under conditions when the spinal cord is at its most ventrally displaced position within the spinal canal.

The surgical opening should provide access for forceps and a needle driver, around the entire circumference of the dural cuff. The device placement and closure technique should be efficient, with no unnecessary steps. The surgical technique can be designed in a manner that minimizes the risk of injuring the spinal cord or damaging or displacing the electrode array from its optimal location. A technically competent neurosurgeon should be able to complete the implantation procedure safely and reliably.

FIGS. 4A to 4E are side views that illustrate a step-wise procedure by which the device may be installed into an operative position on the spinal cord. FIGS. 5A to 5C show the procedure from a top-down view. In FIG. 5A, the solid line labeled 23a is the edge of reflected spinal canal dura. The dashed line labeled 14a is the caudal edge of the dural cuff. FIGS. 6A to 6D are magnified lateral views showing details of how the device is positioned to optimize pressure of the electrode bearing portion on the spinal cord. In these illustrations, the securing strap is shown as a substantially rectangular shape and secured to each of the two vertebral lamina by way of two surgical screws on each side. The device positioning apparatus (DPA) 31 is shown with an affixed (non-retractable) distance measurement extension (DME) 37.

The connecting member 15 of the electrode array support device is secured to the strap 41 at or near the midpoint between the sides that span the lamina at or near the rostral edge of the strap. This can be done, for example, using sutures, small clamps, or an adhesive such as silicone. There may be a portion of the strap designed to accommodate the lead and the suture or clamp. The components are configured so that the device may be positioned to press the electrode bearing portion 11 on the spinal cord 21 at a desired pressure, and then secured in this position by way of the strap 41 or attachment portion.

The steps of the procedure are as follows.

Step 1: A multi-level laminectomy is performed.

Step 2: A mid-line durotomy is created of sufficient length.

Step 3: The device is loaded onto the DPA. This requires looping a suture through the DPA eyelets and around the lead, and then securing the suture on the DPA handle using sufficient tension.

Step 4: The DPA is attached to a malleable retractor arm (modified Greenberg), and the surgeon uses his left hand to move the DPA into position. The retractor is kept on the flexible setting (maximal malleability) until the surgeon has the DPA and attached device in the desired position. Once the device is in the optimal position, an assistant secures the retractor arm to achieve rigid fixation of the DPA and device.

Step 5: Using forceps held in his or her right hand, the surgeon grasps the caudal portion of the device dural cuff and reflects it upward to allow clear visualization of the electrode bearing portion of the device.

Step 6: The DPA is adjusted so that the electrode bearing portion of the device is positioned on the dorsal spinal cord symmetrically between the left and right dorsal root entry zones.

Step 7: The DPA is then lowered further towards the spinal cord causing the intradural leads to bow outward. This compression maneuver is continued until the DME makes gentle contact with the electrode bearing portion of the device. This is then the optimal position for the device assembly.

Step 8: The assistant adjusts the malleable retractor setting to lock the retractor (and the attached DPA) into the optimal position.

Step 9: The surgeon sutures the accessible edge of the dural cuff to the spinal canal dura. The surgeon's line of sight at this stage in the procedure is from a caudal vantage point. Approximately 80% of the circumference of the dural path is sutured to the spinal canal dura from this surgical angle. The only portion of the dural cuff that is not sutured closed is the portion obscured by the section of the DPA that extends rostral from its point of fixation with the device lead.

Step 10: The strap is secured to the device lead and then secured to the left and right edges of the laminectomy defect using bone screws. This step secures the device assembly into its final position relative to the spinal canal.

Step 11: The suture securing the DPA to the device assembly is cut, disconnecting the DPA from the device lead.

Step 12: The surgeon holds the DPA as an assistant changes the retractor arm to the malleable setting. The surgeon then gently rotates and lifts the DPA out of the surgical cavity. Care is taken to remove the DPA from the subdural space without impacting the device assembly or damaging the intradural leads.

Step 13: The surgeon shifts his line of site in order to optimally visualize the rostral portion of the dural cuff. This portion of the dural cuff is sutured to the spinal canal dura.

Step 14: The remainder of the wound closure is carried out in a manner similar to that used for a standard spinal cord stimulator placement operation.

In Steps 7 and 8, the surgeon has an opportunity to optimize the pressure of the array on the spinal cord so that the device accommodates movement of the spinal cord, but without injuring the spinal cord or causing inflammation. Depending on the nature of the device and the judgment of the surgeon, a suitable pressure could be about 0.1 mm Hg to 25 mm Hg. The upper limit (25 mm Hg) is about half of a typical low range human diastolic blood pressure, so that blood flow through surface vessels on the spinal cord would not be choked off by the pressure applied to them by the electrode-bearing surface.

Securing the Electrode Array to the Dura

As an alternative to securing the electrode array to the vertebra, it can be secured to the margins of the dura. There are several advantages of this approach. Surgical implantation of the device may be less cumbersome for some patients. A simple, one-piece device is placed on the surface of the spinal cord, and allowed to expand to engage the dura. No clips or screws are required, and lead manipulation is minimized. Furthermore, the device can be extracted or repositioned more easily. By compressing the device laterally, it disengages from the dura and can be removed from the patient or reengaged elsewhere. This may be an easier surgical procedure that is less likely to cause damage than using clips, clamps, tabs, fusions, or other attachment means and procedures.

This section describes and illustrates a device of this nature and explains how it may be implanted onto the spinal cord of the patient. The features shown in the illustration are not meant to be limiting unless explicitly or otherwise required.

FIG. 7A shows an oblique view of the device before implantation onto the spinal cord of a patient. An electrode bearing portion 11 bears an array of electrodes that face downwards, thereby being configured for direct communication with the spinal cord 21 so that the electrodes may provide electrical stimulation to the region of the cord upon which it is laid. The electrode bearing portion 11 has extensions 17 that extend laterally in both directions, so as to join with the support structure 10. The plane of the electrode array also typically comprises electronic circuitry to create or convey a pattern of electrical stimulation (not shown). Power and control signals may come to the electronic circuitry through a wire connection that passes outside the device, or it may be received through an antenna in the device by wireless transmission.

The support structure 10 shown here is in the form of a half-oval scaffold (HOS). The function is to secure the array 11 to the left and right lateral margins of the dura upon implantation into the spinal canal. The HOS is slightly compressed during surgical insertion. When the HOS is released, small securing pins 18 on each side attach to sites on the left and right lateral martins of the spinal canal dura. The electrode bearing portion 11 is suspended between each side of the support structure 10 by way of extensions 17 of the backing material that extend laterally from the electrode bearing portion 11. Because of their positioning during implantation, the lateral extensions 17 may be referred to as "artificial dentate ligaments".

The embodiment shown here further comprises a dural cuff 14. This can be used to fix the device to a third point of the dura: specifically, the site of the dorsal durotomy closure. Fixation of the cuff during implantation can achieve a water-tight dural closure around the connecting member 15 containing electrical leads, as it exits the dura.

FIG. 7B shows the prototype device in cross-section as it would be implanted onto a spinal cord 21 (shown with white matter 21a and gray matter 21b). The electrode-bearing portion 11 directly contacts the spinal cord, providing a medium through which electric stimulation may be provided. The electrodes are imbedded in a compliant backing of an elastic or pliable backing material so that the array may conform to the spinal cord 21 at a region where the clinician desires to provide an electrical stimulus. The electrodes are exposed downwards to engage the spinal cord such that all or most of the electrodes remain in contact with the spinal cord providing a conduit for imparting the electrical stimulus.

Situated above the electrode bearing portion 11 in this illustration is a support structure 10, shown here curved nominally in the shape of a half oval. The support structure is typically made of a material that is pliably more rigid than the backing for the electrodes. This enables the structure to resiliently support the electrode array, and provide an outward pressure (when laterally compressed) to urge the sides towards the dura, thereby engaging the inner margin. In this example, the backing of the array assembly has extensions 17 (the artificial dentate ligament) that extend towards the support structure 10 on each side, thus anchoring the array downwardly upon the spinal cord 21.

FIG. 7D provides a detail of the securing pin 18 engaging the dura 23 on the left and right margins. FIG. 7C provides a detail of the third fixation point. The dural cuff 14 disposed above the support structure 10 is sutured or otherwise fixed to the dura 23 at an incision point, such as may be generated by surgical insertion of the device. In this illustration, a connecting member or sheath (not shown) passes through the dural cuff 14 and out of the spinal canal, carrying leads 16 to an external component that supplies power and control signals to electrodes in the electrode bearing portion 11.

FIG. 8A shows the implanted device in a top down view. The dura 23 is shown in transverse cross-section. The electrode bearing portion 11 is attached to the support structure 10 by way of the backing extensions 17, with the connecting member 15 exiting the spinal canal upwards. FIG. 8B shows a side view of the spinal cord 21 with the dura 23 in transverse cross-section. The electrode bearing portion 11 is maintained in direct contact with the spinal cord 21 white matter by way of the extensions 17 attaching to the support structure 10 at or around the point where the pins 18 secure the support structure to the dura 23.

Installation of the Device

The device may be affixed to the dura by way of contact points that adhere to or transverse the dura. Alternatively, the device can be constructed in such a fashion that its sides span the width of the spinal canal, and/or maintain a gentle lateral pressure so as to secure the device in place.

Figure 9A:
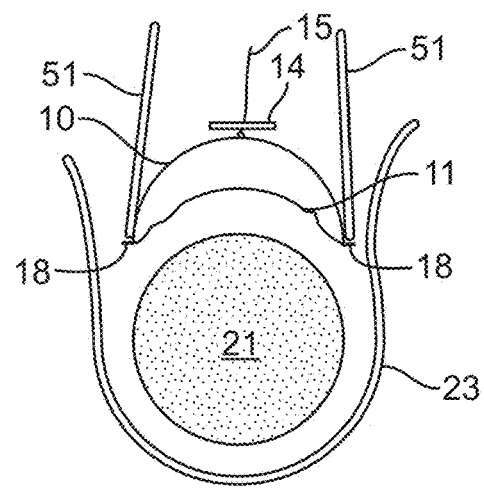
Figure 9B:
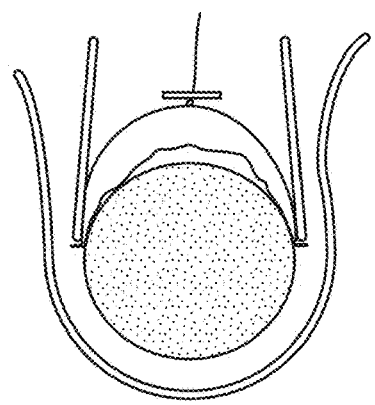
Figure 9C:
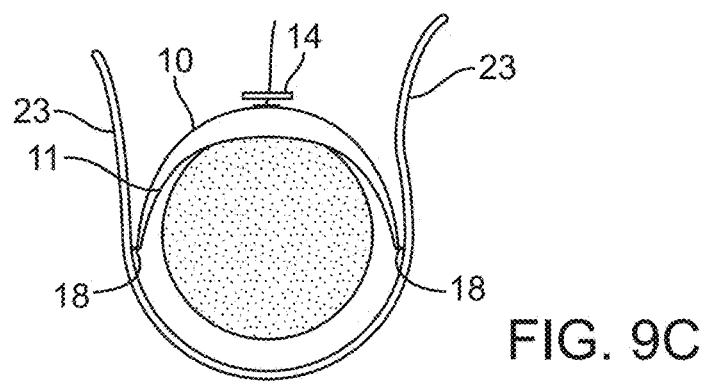
Figure 9D:
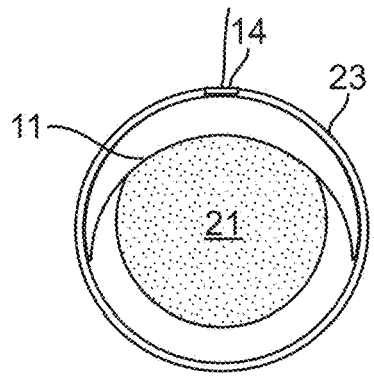

FIGS. 9A to 9D show how the device may be implanted such that the electrodes are put in contact with the spinal cord 21. In FIG. 9A, an incision is made in the dura 23 from the dorsal side that is large enough for the compressed device to be introduced into the spinal canal. The device comprising the electrode bearing portion 11 and the support structure 10 is compressed inwardly by way of forceps 51 that are specially designed to configure to the sides of the device and compress the sides and hold the device in the compressed or smaller configuration. In FIG. 9B, the electrode array is passed through the incision and positioned over the exposed dorsal surface of the spinal cord. In FIG. 9C, closing tension on the forceps is reduced, allowing the support structure 10 to expand laterally, thereby urging the dural securing pins 18 into the dura 23. In FIG. 9D, the dura 23 is closed, incorporating the device's dural cuff 14 into the closure. Each contact point with the dura may have a plurality of pins, a pad, a smooth or rough surface integral to the extension or support structure, or a contact feature is discrete and mounted onto the device, facing outwards towards the dura. The pin or other contact feature may be configured to engage the dura without rupturing the surface, or it may pass into or through the dura, optionally to be secured on the other side with a cap.

Securing the Electrode Array to the Dentate Ligaments

Alternatively or in addition to securing the electrode array to the vertebra and/or the dura, the device may be secured to or otherwise placed in communication with the dentate ligaments. One normal function of the dentate ligaments is to suspend the spinal cord within the spinal canal in a physiologic manner that enables supple movement of it but does not cause chronic injury to the spinal cord from mechanical tethering.

FIG. 10A shows an electrode array adapted for clamping to the dentate ligaments. The device has an electrode bearing portion 11 supported by a support structure in the form of a body 12a which includes a flexible substrate or backing, with the array configured to engage a dorsal portion of the spinal cord 21. Dentate ligament attachment features such as flexible arms 17a extend laterally from left and right sides, with the arms optionally comprising the same substrate or backing material from which the body is formed. The extensions are configured to be attached to left and right dentate ligaments 28 on either side of the treatment region of the spinal cord to secure the electrode bearing portion 11 in engagement with the spinal cord. The attachment arms 17a may be more elastic than the array backing, extending laterally from the electrode array. The attachment arms 17a may flair to a larger width adjacent the ends opposite the array, or may have slightly raised groves or texture at or near these ends to facilitate clipping, crimping, or adhesively bonding the arms to the dentate ligament. FIG. 10B shows a detail of the clip or tab 19 used to attach the arms 17a to the dentate ligament 28.

Electrode Design

FIG. 11A schematically illustrates an electrode projecting from an interior surface of a backing or substrate. Therapeutic benefit may be enhanced by maximizing current densities in the targeted conducting tracts of the spinal cord itself, while minimizing the current density shunted away by the CSF. In this embodiment, the electrodes are engaged against the surface of the spinal cord as shown, with a stand-off column 62 extending between the exposed portion of the electrode 61 and the underside of the electrode backing 64. This arrangement can support the implant off the surface of the spinal cord by about 100 µm to accommodate pulsation of the spinal cord 21. By insulating the surface of stand-off column 62, it is possible to minimize the shunting effect of the CSF, since the exposed portion of the electrode will be in contact only with the pial surface of the spinal cord 21, and not with the CSF itself. Gentle inward pressure causes slight inward "dimpling" of the pial surface by the electrode. As a result, the active exposed surface of the electrode is "sealed" by spinal cord tissue enveloping the protruding portion of the contact. A small gap separates the electrically inactive portions of the array, providing space into which the spinal cord tissue may expand and contract with cardiac pulsation cycles.

FIG. 11B schematically illustrates individual electrodes 61 flexibly mounted to a substrate or backing 64 by a soft resilient material 65 so as to allow the electrode to resiliently float or move radially and/or laterally relative to the substrate by a distance that is at least as large as the pulsations of the surface of spinal cord 21. This movement of each electrode may inhibit sliding engagement of the electrodes against the surface of the spinal cord during pulsation or any other type of spinal cord movement. In some implementations, the only parts of the array that directly engage the spinal cord are the electrode contacts. These may serve as mechanical anchoring points for the device. They exert enough pressure to maintain good electrical contact with the surface of the spinal cord. The pressure exerted should be generally even for all of the contacts, for example, by having electrodes protruding slightly from contoured attachments arms (not shown). This places all contacts in the desired position in relation to the surface of the spinal cord. Outward and inward movements of the contacts (e.g. with pulsations and respirations) are accommodated by movements of the semi-rigid attachment arms.

The bodies of the electrodes 61 extend through apertures 66 in substrate or backing 64, with the substrate being pliable and having elasticity appropriate to supporting thin film circuit components. A soft elastomeric material 65 spans the apertures from the backing 64 to the electrodes 61, with the elastomeric material here comprising a sheet of material adhered to the outer surface of the substrate. Alternatively, the electrodes 61 may be supported relative to each other and the substrate with a soft elastomeric material spanning directly between the electrode and the walls of the aperture. Alternatively, the electrodes may be supported relative to each other and the substrate with a soft elastomeric material spanning directly between the electrode and walls of the aperture. Flexible conductors (not shown) may extend between the substrate and electrode bodies within or outside the elastic material with these conductors optionally being serpentine, having loops, or otherwise configured to accommodate movement of each electrode body relative to the substrate.

As shown in the figure, the electrode bodies 234 extend through apertures 238 in substrate 230, with the substrate being pliable and having elasticity appropriate to supporting thin film circuit components. A soft elastomeric material 236 spans the apertures from substrate 230 to the electrode bodies, with the elastomeric material here comprising a sheet of material adhered to the outer surface of the substrate. Alternatively, the electrodes may be supported relative to each other and the substrate with a soft elastomeric material spanning directly between the electrode and walls of the aperture. Alternatively, the resilient material may form column 220. Flexible conductors (not shown) may extend between the substrate and electrode bodies within or outside the elastic material with these conductors optionally being serpentine, having loops, or otherwise configured to accommodate movement of each electrode body relative to the substrate.

Other Features of the Electrode Array

A support device according to this invention presents an array of electrodes configured to conform to a region of the spinal cord such that the electrodes directly contact the spinal cord. Suitable electrode arrays are described below and in WO 2012/065125. A compliant backing is typically used, and is reshaped with a curvature to lie on top of the dorsal aspect of the spinal cord so that the electrodes across the array are in contact with the dorsal pial surface of the spinal cord surface.

An implantable device according to this invention comprises a plurality of electrodes for placing in direct contact or electrical communication with the pial surface and underlying white matter of the spinal cord, within the spinal canal. The electrodes may be arrayed on a pliable background, constructed of a material and in a shape that allows it to be conformed directly to the spinal cord. The plurality of electrodes may comprise at least 10, at least 20, at least 30, or at least 50 electrodes. They may be arrayed on the backing in a grid, a rectilinear pattern, or any other arrangement that is effective. All of the electrodes may be supplied with stimulating power through a common lead. Alternatively, the electrodes may be attached singly or in groups to separate leads so that each electrode or electrode group can provide the spinal cord with a separate stimulus as programmed by a central control unit.

Array Design

The electrode bearing portion (EBP) of the array is generally structured to conform to the dorsal surface of the spinal cord and maintain each of the electrodes in contact so as to deliver an electrical signal. Suitable parameters for the array may be drawn from Example 1, below. The array may be provided in a range of stock sizes. Alternatively, it can be custom manufactured according to the anatomy and treatment objectives for each patient. The exact anatomical dimensions of a given patient's dorsal spinal cord can be determined from a pre-operative MRI study. The EBP is manufactured to be semi-rigid and have a fixed curvature that is appropriate for a given patient's spinal cord.

The array will be held in place by forces exerted by a plurality of leads spanning the space between the EBP on the spinal cord surface and the dura. The direction and magnitude of forces exerted on the EBP will vary significantly as the spinal cord moves within the spinal canal. In some extreme spinal cord positions there will be a tendency for the lead forces to cause the EBP to lift or rock out of position. This effect can be reduced by adding non-lead bearing physical extensions to the EBP. Extensions of semi-rigid silicon in both the rostral and caudal directions make the EBP less likely to lift off of the spinal cord surface when the cord is displaced. Similarly, laterally positioned extensions help prevent lateral slippage. These extensions may be referred to as "outriggers". The configuration of the electrodes on the array and the stimulus patterns used to energize them may be selected to optimize the distribution of electrical current density within the target tissues of the spinal cord, while minimizing the spread of said electrical current density into non-targeted tissues, for example the dorsal root entry zones.

Electrical Leads

Where the device receives power or control signals from an external source by way of wire leads, the leads pass through the dura to be in electrical communication with the circuit and the electrodes. By providing the leads with a cuff, flange or other feature for attachment to the dura where the leads pass through, a fixation point for the device is created by attaching or sealing the feature to the dura. After passing into the spinal canal, the leads may trace a path along the extensions or support structure (either internally or on either side), and then continue to the circuit or electrode array.

Lead segments between the electrode array and the dura may be configured to serve at least two functions. One is to conduct electrical signals; the other is to exert the desired physical forces on the EBP to maintain its optimal position on the mobile spinal cord: specifically, a gentle, stable pressure on the EBP for a wide range of spinal cord positions. Long, looping leads can be used that are oriented predominantly in the rostro-caudal plane, but with a slightly oblique orientation to deliver some components of force in directions that help prevent left-right migration of the EBP along the surface of the spinal cord, or torqueing of it about the axial direction. These leads flex and extend as the cord moves within the spinal cord. A preferred material for the leads is a highly malleable, braided lead made of a superalloy (MP35N/silver-core DFT wire stranded cable).

If a lead were to break, it would be better for this to occur in such a way that the repair procedure does not require that the intradural portion of the device be replaced. As shown in FIG. 15, a design feature to address this issue is to place a connector 82 on a first lead portion 81 located close to where the first lead portion exits the dura. A relay or second lead portion 82 is then used from that point to the stimulus delivery unit located in the external component 84. The overall system is thereby configured so that, if a lead break were to occur, it would be much more likely to occur in the relay than in the intradural portion of the device.

Device Components and Commercial Distribution

A device according to this invention may be part of a system that also comprises external components: particularly a power supply, and a control unit that sends control signals to the circuitry or electrodes on the implanted device. This is shown in FIG. 15. The external component 84 may provide both a power source and electronics for controlling the electrical stimuli. There may be a microprocessor or other suitable controller that is programmed to shape the electrical stimuli into one or more particular patterns, and to regulate the frequency of an alternating current. The external component of the device may be configured to receive operator input regarding stimulus pattern selection and/or amplitude and frequency. Alternatively or in addition, the external component may also be configured to receive feedback data and to adjust the pattern and/or amplitude and frequency to improve the effect perceived by the patent.

Optionally, the circuitry controlling the stimulus supplied by the electrodes may be built into the same backing as the electrodes. Power and control signals can be provided to the circuitry and the electrodes by electrical leads that pass in and out through the dura. Alternatively, the device may have a receiving means such as an antenna through which to receive power and control signals wirelessly from an external source.

The device and technology of this invention can be used for diagnostic, therapeutic, and research purposes in human subjects, primates, and other domesticated and non-domesticated mammals. Upon determination that a patient or other subject would benefit from electrical stimulation from a device according to the invention, the clinician would first implant the device onto the spinal cord. The location may be predetermined by imaging the spine and/or doing neurological studies, and then selecting a location that would be most likely to convey the desired benefit.

For some purposes, the device may be supplied from the manufacturer in a standard size that can accommodate almost the full range of spinal cord anatomy variations encountered in patients. Alternatively, the device can be built in a plurality of different standard sizes, or may be custom manufactured for particular patients. In these circumstances, the method of installing the device would further comprise the step of determining appropriate dimensions of the patient's anatomy (such as circumference or cross-sectional shape of the spinal cord and/or the spinal canal on the dorsal side, and/or dimensions of the vertebra to which the device is to be secured.

Clinical Use

The device is implanted by conforming the arrayed electrodes to a region of the spinal cord so that the electrodes directly contact the spinal cord; and then securing the device in place. Once fixed in place, it remains after surgical closure, and maintains the electrodes in contact with the spinal cord, notwithstanding normal pulsation and mobility of the spinal cord, movement of the patient in ordinary daily activity, and movements resulting mechanical such as might result if the patient slips or falls. The affixing of the device, while robust, is preferably reversible so that the device can later be removed or repositioned if needed, while causing minimal damage to the tissues.

Once implanted, the electrode array can be used for stimulating a spinal cord of a patient. The patient may be subject or susceptible to noxious or deleterious nerve signals transmitted along the spinal cord, or otherwise requires treatment. An electrical stimulus is provided through the electrodes in the array directly to the spinal cord so as to inhibit transmission of such noxious or deleterious nerve signals.

The stimulus may be applied to inhibit sensation of pain, or to inhibit symptoms or sensory input that is undesirable or disruptive to the patient, either in the back itself, the extremities, or at another location wherein the pain is mediated at least in part by the spinal cord. Conditions suitable for treatment include back pain, leg pain, Parkinson's disease, spinal cord injury, Failed Back Surgery Syndrome, arthritic degeneration, phantom limb pain, numbness or palsy, or congestive heart failure. The stimulus may be provided to the spinal cord by the device on a constitutive basis, in response to feedback data, or it may be subject to the patient's conscious control.

The treating clinician may select any electrical stimulus that is effective in managing pain of a particular patient. The general object is to induce refractoriness of the spinal cord to transmit noxious or deleterious signals or synchronous depolarization events initiated locally. This can be adjusted empirically by determining neural activity and recording the symptoms experienced by the patient Different patterns of stimulation may be effective depending on clinical circumstances. Under control of an appropriately programmed microprocessor or any other suitable type of controlled signal generator, electrodes in the array may all provide the same signal pattern, or individual or groups of electrodes may have their own signal pattern configured to work independently or in concert with signal patterns of other electrodes in the array.

The electrical potential may vary at a regular frequency in a sinusoidal or square wave form. Alternatively, the wave form may be a more complex pattern, with pulses appearing at varying intervals and intensities according to a calculated or repetitive pattern. Such patterns comprise a pulse train generating substantially continuous activation of nerves within the spinal cord, and may incorporate irregular pulse intervals, irregular pulse amplitudes, a variety of wave forms (for example, monophasic, biphasic, rectangular, sinusoidal, as well as asymmetric or irregular wave forms), or any combination thereof. The potential may create what is essentially a broad band noise, varying at stochastic or essentially random intervals and intensity under the influence of a suitable computational algorithm or automated control program in a microprocessor.

Depending on the objective of the treatment and the manner in which the technology is deployed, effective pulse repetition rates or frequencies may be at very low frequencies, or above 100 Hz (pulses per second), or at higher frequencies to cause stochastic depolarization, as described below.

High Frequency Stimulation to Cause Stochastic Depolarization

High frequency stimulation of the spinal cord may benefit the patent by inducing a state of pseudospontaneous axon firing. Bundles of sensory axons are thought to fire randomly when not transmitting sensory stimulus. When a sensory stimulus is presented, a substantial proportion of the axons within a bundle or pathway will discharge in a synchronous fashion—firing axons potentials at about the same time. This results in the sensory input being transmitted along the axons in the bundle, so that the subject may experience the sensation. Stated differently, the absence of sensation is coded by random timing of axon firing within a bundle, whereas a sensory perception is coded by synchronous firing of a population of axons.

It is a hypothesis of this invention that patients with leg and back pain have bundles of axons spontaneously firing in a synchronous manner (or some other non-random fashion), instead of the normal random pattern of firing. Electrical pulses will entrain axonal firing. A single pulse delivered to a bundle of axons will cause them all to fire synchronously. If the time interval between each electrical shock in a pulse train is longer than the refractory period of the axons in the bundle, each subsequent shock will also synchronously activate all of the axons, and a subject will experience a sensation. A low frequency alternating current applied to the back (50 Hz) may be effective in reducing the sensation of pain, but the stimulation may generate neurological side effects such as paresthesias (tingling or numbness).

A high frequency electrical stimulus (say, about 5,000 Hz) has interval spacing shorter than the refractory period of axons. An individual axon cannot fire again in response to a second shock until its membrane potential has recovered from the effects of the first shock, and this takes time. Different axons have different refractory periods. By delivering electrical pulses at high frequency, the relative timing of firing by individual axons within the bundle of axons becomes nearly random, with different axons become excitable again at different times. Applying high frequency pulses to the spinal cord can be used to restore a state of active quiescence in the sensory nerves passing through the cord.

Put another way, the spinal cord is stimulated so as to inhibit pain transmission by applying directly to the spinal cord an electrical stimulus that renders sensory neurons refractory to transmission of synchronous action potentials initiated within the spinal cord. This inhibits back pain from locally induced sensory input, and side effects such as paresthesia that may be induced in the course of local treatment. The electrical stimulus is thought to promote stochastic depolarization of sensory neurons within the spinal cord, thus inducing a state of neural quiescence.

To accomplish this, the electrical stimulus comprises a potential that alternates at high frequency. Regardless of the way the potential may vary over time, the frequency may be calculated by determining the number of positive-to-negative alterations per unit time. Effective frequency ranges depend on place of placement of the electrode array, the features of the array, the nature and health of the tissue where the array is placed, and the objectives of treatment. The general object is to induce refractoriness of the spinal cord to transmit deleterious signals or synchronous depolarization events initiated locally. This can be adjusted empirically by determining neural activity and recording the symptoms experienced by the patient.

Depending on the objective of the treatment and the manner in which the technology is deployed, effective pulse repetition rates or frequencies may be at or above 100 Hz (pulses per second), 200 Hz, 500 Hz, 2,000 Hz, or 5,000 Hz, a frequency of about 1,000 Hz, 4,000 Hz, or 10,000 Hz, or a frequency range of about 500 to 50,000 Hz, 1,000 to 9,000 Hz, 3,000 to 8,000 Hz, 2,000 to 20,000 Hz, or 5,000 to 15,000 Hz.

Treating back pain according to the invention may comprise administering an effective electronic stimulus to the spinal cord, monitoring transmission of synchronous action potential through the spinal cord or inferring the same, and then adjusting the electrical stimulus so as to further inhibit transmission through the spinal cord of synchronous action potentials. The electrical stimulus may be adjusted in frequency or other waveform parameters and manner of application so as to minimize side effects such as paresthesia, and to minimize impact on transmission of essential neurological faction, including motor neuron activity, and nerves involved in proprioception and kinesthesia. Optionally, the clinician or the user may be provided with an input or control means to select the pattern, adjust the frequency, and adjust the intensity in accordance with the perceived symptoms.

EXAMPLES

Example 1: Optimization of the Electrode Array Structure Using Thoracic Spine Imaging Data An important dimensional parameter for a spinal cord stimulator array is the arc length that it subtends over the dorsal surface of the spinal cord. There are conflicting design goals. One is to make that span as long as possible, in order to maximize the number of electrodes and hence the stimulus-pattern coverage of the underlying dorsal columns. However, another is to ensure that the membrane does not make mechanical contact with the dorsal rootlets.

In this study, structural dimensions of the spinal cord at the level of the $4^{th}$ through $10^{th}$ thoracic vertebrae were investigated (the region in which the array should be placed when treating back and leg pain). The arc length "S" between dorsal-root entry zones (DREZ) was calculated in two ways from magnetic resonance (MR) images of the thoracic spine for 50 patients seen at the University of Iowa Hospitals and Clinics.

One axial and sagittal image from each patient was selected for analysis. The available images covered the range T4 through T10 from high-resolution MR scans of both male (ages 17 to 77 years) and female (ages 20 to 84 years) patients. The imaging studies had been ordered by clinicians to rule out pathological processes affecting the spine, and in all cases studied no pathological abnormalities were noted. All of the subjects were imaged in the supine position in a straight posture without any bending or flexing of the legs, hips or spine. Of the selected slices, 70% (n=35) were at either T7 or T8 which will be the preferred location for positioning the array in most patients. The remaining images were distributed above and below that zone to help insure a representative assessment.

With reference to FIG. 12A, the bi-lateral locations of the dorsal root entry zones, $P_1$ and $P_3$, were identified by neurosurgeons on each of the 50 axial slices, and the linear separation, A, between them was measured relative to the calibration scale bar on each image. The distance, B, between the center of that line and the dorsal-most point of the spinal cord, $P_2$, was also measured, as were the maximum sagittal and coronal diameters of the spinal cord (i.e., the minor and major axis diameters, respectively). The resulting data were then archived for subsequent analysis, with the primary goal being to determine the peripheral arc length, S, connecting the points $P_1$, $P_2$ and $P_3$.

The cross section of the spinal cord in the thoracic region is roughly oval in shape, but with an irregular circumference that departs from an ellipse. S was estimated by computing the hypotenuse to the triangle formed by A/2 and B: $S_H \approx 2 \cdot [(A/2)^2 + B^2]^{1/2}$. Because the actual arc rises just above that hypotenuse, $S_H$ slightly underestimates S. Alternatively, with reference to FIG. 12B, S was estimated by way of the circular arc length: $S_R \approx r \cdot \theta$, where r is the estimated value of radial distance between the geometric center of the spinal cord and the points $P_1$ and $P_3$, and $\theta$ is the angular separation between those lines. Because the actual arc lies below the circumscribing path of $S_R$, this calculation slightly overestimates S.

Thus, $S_H < S < S_R$. Measurements to confirm this and establish the most likely value of S within that range can then be made directly on a magnified view of an axial image, using a flexible rule and the appropriate scaling factor to determine the distance along the span. The estimate of S, as determined across the entire patient population, can be used as a design guide for the membrane length of the patch. The value of "r" determined from the measured major and minor axis diameters, can then be used to establish the radius of curvature for the array membrane.

The measured values of A and B in mm were as follows: All patients (n=50), 5.8±0.8, 1.5±0.4; males (n=34), 5.9±0.8, 1.5±0.4; females (n=16), 5.5±0.7, 1.5±0.4 The relative uncertainties (standard deviation÷mean) in the values of A and B across all patients was 14% and 27%, respectively. The value of A across all male patients was approximately 2% larger than the mean for all patients, and that for the female patients was approximately 5% smaller. The calculated value of $S_H$=6.5±1.2 mm. The difference between the largest mean value of $S_H$ (8.8 mm) and the smallest (5.1 mm) was 3.7 mm—approximately three times the size of the standard deviation (1.2 mm), indicating that this is a dimension of the neuroanatomy in which significant outliers occur.

The sagittal and coronal diameters of the spinal cord in each of the 50 axial images were 6.2±0.6 mm and 8.3±0.8 mm respectively. Thus, the mean radius and quadratured-sum uncertainty of the spinal cord is r=3.6±0.5 mm. Upon review of other results, it seemed most conservative to take r=4.1 mm to be the working value of the mean radius. Using $\theta \approx 95°$, $S_R$=6.8±1.0 mm, where the uncertainty is given by the quadratured sum of those measured for r and estimated for $\theta$.

The calculated values of $S_H$ and $S_R$ were compared against physical measurements made with a flexible rule laid carefully along the dorsal arc pathway of images expanded 3-fold. The length of the dorsal arc span between the rootlet entry zones was estimated to be S=6.7±1.0 mm.

Thus, if the width of an electrode array was were 6.7-1.0=5.7 mm, then it would be a good fit to the spinal cords of at least 68% (1σ) of the patients receiving the implant. The problem would come with the outliers at the high and low ends of the distribution of arc lengths. Providing three different widths of 8 mm, 6 mm and 4 mm would be suitable for substantially all the adult population. The largest size device would have additional electrode contacts and leads.

Alternatively, custom arrays could be fabricated for individual patients using patient-specific arc length measurements.

The mean radius of the spinal cord across all patients was r=3.6±0.5 mm. A nominal mean value of r=4.1 mm would be suitable for curvature of the array. Opting for a slightly larger radius of curvature reduces the risk of spinal cord compression that might arise from too small a sizing.

Example 2: MR-Based Measurement of Spinal Cord Motion During Flexion of the Spine: Implications for Intradural Spinal Cord Stimulator Systems For purposes of this study, a 1.5 T Magnetom Espree® magnet (Siemens, Erlangen, Germany) was used. Informed consent was obtained from healthy volunteers ranging in age from 23 to 58. Each volunteer was first imaged in a supine neutral position and then imaged in a maximal attainable flexed position.

To obtain the maximal flexion of the spine, patients were given three basic positioning instructions. The first was to rotate their pelvis backwards towards the gantry as far as possible to remove the lumbar lordosis and straighten the lumbar spine. The second was to curl their upper back, neck and head forward so that their shoulders were as close to their knees as possible. The third instruction was then to tuck their chin down as close to their chest as possible. While attaining this flexed position in the bore, a variety of foam wedges and pillows were used for added support so that the patient could remain as still as possible during image acquisition. Maximal flexion was limited by volunteer flexibility in 14 of the patients. In only two patients was flexion limited by MR bore size.

Each volunteer had a vitamin E capsule taped to their midline lower thoracic spine for help in level localization. A sagittal HASTE sequence was performed initially as a localizer both for vertebral level counting and identification of a more focal field of view centered over the region of lowest thoracic spinal nerves and the conus medullaris. To acquire anatomic images with enough resolution to accurately measure intervals between spinal nerve dorsal root entry zones, a CISS sequence was selected for its high spatial resolution. Although this is a highly T2-weighted sequence, acquisition time still required 2 minutes and 5 seconds. This length of time initially caused too much motion degradation during flexed imaging to make accurate measurements. The use of the pillows and foam wedges provided just enough support for volunteers to remain still for the required two minute duration. All neutral and flexed sequences were obtained using TR=4.35 ms, TE=2.18 ms, slice thickness=0.8 mm, matrix size=192×192, one acquisition per average, 192 phase encoding steps, field of view=200 mm, and a 70 degree flip angle.

FIG. 13B shows an example of a coronal image on which the relevant anatomical features are identified. Imaging was obtained in the coronal plane. Three-dimensional multiplanar reconstruction software was used on a Carestream PACS station to aid in measurement. The T10 and T11 nerve roots were identified. A cranial caudal measurement was made in a plane parallel to the spinal canal between the dorsal-root entry zones (DREZ) of T10 and T11. (The exact position of the entry zones was confirmed by assessing sequential axial images to identify the most cranial aspect of the nerve originating from the spinal cord.) As shown in FIG. 13A, the difference between this measurement on the neutral and flexed images is a measure of spinal cord contraction/expansion along the rostral-caudal axis. Next, a cranial caudal measurement was made from the DREZ of the T10 nerve root along the same plane as the prior measurement, to the level of a plane orthogonal to the spinal canal at the level of the inferior T10 pedicles. The latter were selected as a reference point of the bony canal inside of which the spinal cord moves. The difference between these measurements represents cord movement within the bony canal.

A cranial caudal measurement of the change in conus tip position was made. To accurately accomplish this, the position of the conus tip was first identified on the neutral images with reference to a landmark within the bony spinal canal at the same cranial-caudal level. This landmark was then identified on flexed imaging and a cranial caudal measurement was made from that level to the level of the new conus position. This represents movement of spinal cord within the canal.

Results were as follows. The spinal cord should move rostrally during flexion and should lie in its most caudal location when the patient is in the neutral position. The measured change in the pedicle-to-spinal cord DREZ distance across all patients between the neutral and flexion positions ranged from 1.9 mm to 18.0 mm, with a mean and standard deviation of 8.5±6.0 mm. The inter-DREZ distance across all patients between the neutral and flexion positions ranged from −2.0 mm to +6.7 mm, with a mean and standard deviation of 3.5±2.6 mm. The mean and standard deviation for the rostral-caudal conus movement was found to be 6.4±4.1 mm within an overall range of 1.1 to 11.4 mm. The fractional variations in these findings (standard deviation÷mean) are very large, 71%, 74% and 64% respectively. This reflects the wide variability in the capacity of individual subjects to maximally flex the spine, as well as possible inter-subject variability in spinal cord mechanical characteristics. These findings highlight the need for the device to accommodate larger patient-to-patient variations in spinal cord dynamic movement properties.

The ratio of the spinal cord's mean stretch-to-mean axial movement over a full flexion cycle was 3.5 mm/8.5 mm≈40%. On average across all patients, it required 1 mm of net axial displacement of the cord to stretch it 0.4 mm in length. A spinal cord stimulator device should accommodate a total rostral-caudal motion of up to ~2 cm of the cord/membrane relative to the fixation point, i.e., 1 cm rostral and 1 cm caudal from the neutral position.

A prototype device of the type shown in FIG. 14 (loop area 160 mm$^2$) was used to test the available range of motion. It comprises an analogue electrode bearing portion 11 without electrodes, a spring portion 12, and a securing strap 41. The prototype device was placed on a custom-designed silicone surrogate spinal cord specimen that was positioned inside an anthropomorphic spinal canal phantom (not shown). The device was able to accommodate this level of motion without lift-off of either end of the membrane when the surrogate reached the 1 cm rostral and caudal extremes of displacement.

Since there were large variations (70%) in the magnitude of that motion from patient to patient, there will be a spectrum of spinal cord strains associated with flexion-driven motion of the cord. Having suitable axial compliance within the electrode bearing portion of the device will reduce the risk of potential irritation of the pial surface in patients where the intraparenchymal strains are large. In patients with small levels of strain, there would be little relative motion between cord and the array, meaning that there would be small risk of any skidding between them. The net axial travel of the spinal cord relative to the fixation point is within the range that can be accommodated without lift-off of the electrode bearing portion of the device.

Each and every publication and patent document cited in this disclosure is hereby incorporated herein by reference in its entirety for all purposes to the same extent as if each such publication or document was specifically and individually indicated to be incorporated herein by reference.

While the invention has been described with reference to the specific embodiments, changes can be made and equivalents can be substituted to adapt to a particular context or intended use, thereby achieving benefits of the invention without departing from the scope of what is claimed.

The invention claimed is:

1. A method for stimulating a spinal cord that is prone to transmit deleterious nerve signals in a subject, the method comprising:
   implanting an electrode assembly into the subject at a position between the pial surface of the spinal cord and the dura mater that surrounds the spinal cord, wherefrom the assembly does not obstruct flow of cerebrospinal fluid (CSF) around the spinal cord;
   implanting a signal generator into the subject outside of the dura;
   electrically connecting leads from the electrode assembly through the dura to the signal generator;
   securing the electrode assembly to the dura so as to maintain the assembly at said position; and then
   applying to the spinal cord by way of the electrode assembly an electrical stimulus that pulses or alternates with a frequency at or above 500 Hertz, thereby inhibiting transmission of the deleterious nerve signals.

2. The method of claim 1, wherein the implanting includes securing the electrode assembly to the dura of the spinal cord by a water-tight dura-traversing lead fitting.

3. The method of claim 1, wherein the implanting includes securing the electrode assembly wherefrom electrodes in the electrode assembly are maintained in direct contact with a region of the spinal cord unaffected by movement of the subject.

4. The method of claim 1, wherein the electrode assembly comprises at least 10 electrodes arrayed on a pliable backing.

5. The method of claim 1, wherein the electrical stimulus pulses or alternates at a frequency between 2,000 and 20,000 Hz.

6. A method for inhibiting transmission of deleterious nerve signals through the spinal cord of a subject in need thereof,
   wherein the subject has been implanted with a medical device that comprises:
   (1) an electrode assembly, implanted between the pial surface and the dura mater of the spinal cord and secured to the dura without tethering the spinal cord to the dura;
   (2) a signal generator, implanted outside the dura; and
   (3) leads that electrically connect the signal generator through the dura to the electrode assembly;
   wherein the method comprises applying to the spinal cord by way of the electrode assembly an electrical stimulus that pulses or alternates with a frequency at or above 200 Hertz, thereby inhibiting transmission of the deleterious nerve signals through the subject's spinal cord.

7. The method of claim 6, wherein the electrode assembly has been secured to the dura of the subject by a water-tight dura-traversing lead fitting.

8. The method of claim 6, wherein the electrical stimulus pulses or alternates at a frequency that causes stochastic depolarization of the spinal cord, thereby inhibiting transmission of synchronous action potentials initiated within the spinal cord.

9. The method of claim 6, further comprising adjusting the frequency of the electrical stimulus that is being applied to the spinal cord of the subject.

10. The method of claim 6, wherein the electrical stimulus pulses or alternates at a frequency between 2,000 and 20,000 Hz.

11. The method of claim 6, wherein of the electrical stimulus pulses or alternates at a frequency between 5,000 and 15,000 Hz.

12. The method of claim 6, wherein the amplitude of the electrical stimulus varies in a nonuniform pattern or at stochastic intervals.

13. A method of treating back pain in a subject, comprising inhibiting transmission of deleterious nerve signals through the spinal cord of the subject according to the method of claim 6.

14. An assembly of components for a medical device that is configured for stimulating a subject's spinal cord, the assembly comprising:
   an electrode assembly that has a sufficiently thin profile to be implanted at a position between the pial surface of the spinal cord and the dura mater without obstructing flow of cerebrospinal fluid (CSF) around the spinal cord, wherein the electrode assembly is configured to be secured to the dura so as to maintain the assembly at said position;
   a plurality of electrodes positioned on the electrode assembly that are directed towards the surface of the spinal cord when the electrode assembly is thus implanted and secured;
   electrical leads passing from the plurality of electrodes of the electrode assembly that are electrically connectable through the dura to a signal generator located outside the dura when the electrode assembly is thus implanted and secured; and
   said signal generator, implantable in the subject at a location outside the dura of the spinal cord wherefrom it is connectable by way of the electrical leads to the electrodes of the electrode assembly thus implanted and secured;
   wherein the signal generator is configured to transmit electrical signals through the leads to the plurality of electrodes of the electrode assembly, and thereby to apply to the spinal cord of the subject an electrical stimulus that pulses or alternates at a frequency of at least 200 Hertz.

15. An assembly of components according to claim 14, wherein the electrical stimulus pulses or alternates at a frequency between 2,000 and 20,000 Hz.

16. An assembly of components according to claim 14, wherein the electrical stimulus pulses or alternates at a frequency between 5,000 and 15,000 Hz.

17. An assembly of components according to claim 14, wherein the frequency of the electrical stimulus that is applied to the spinal cord of the subject is adjustable.

18. An assembly of components according to claim 14, wherein the electrode assembly comprises at least 10 electrodes arrayed on a pliable backing.

19. An assembly of components according to claim 14, further comprising a lead fitting that is configured to secure the electrode assembly to the dura to form a water-tight closure, through which the electrical leads from the electrode array inside the dura are connectable to the signal generator outside the dura.

20. An assembly of components according to according to claim 14, wherein the electrical stimulus is adjustable in response to pain experienced by the subject so as to further inhibit transmission through the spinal cord of synchronous action potentials.

* * * * *